United States Patent
Michiyuki et al.

(10) Patent No.: US 11,390,911 B2
(45) Date of Patent: Jul. 19, 2022

(54) METHOD FOR DETECTING A TARGET BASE SEQUENCE

(71) Applicant: EIKEN KAGAKU KABUSHIKI KAISHA, Tokyo (JP)

(72) Inventors: Satoru Michiyuki, Ohtawara (JP); Hidetoshi Kanda, Tochigi (JP)

(73) Assignee: EIKEN KAGAKU KABUSHIKI KAISHA, Tokyo (JP)

(*) Notice: Subject to any disclaimer, the term of this patent is extended or adjusted under 35 U.S.C. 154(b) by 342 days.

(21) Appl. No.: 16/344,413

(22) PCT Filed: Oct. 25, 2017

(86) PCT No.: PCT/JP2017/038458
§ 371 (c)(1),
(2) Date: Apr. 24, 2019

(87) PCT Pub. No.: WO2018/079579
PCT Pub. Date: May 3, 2018

(65) Prior Publication Data
US 2020/0056228 A1 Feb. 20, 2020

(30) Foreign Application Priority Data
Oct. 26, 2016 (JP) .............................. JP2016-209929

(51) Int. Cl.
*C12Q 1/6827* (2018.01)
*C12Q 1/6816* (2018.01)
*C12Q 1/6851* (2018.01)
*C12Q 1/6858* (2018.01)
*C12Q 1/6876* (2018.01)

(52) U.S. Cl.
CPC ......... *C12Q 1/6827* (2013.01); *C12Q 1/6816* (2013.01); *C12Q 1/6851* (2013.01); *C12Q 1/6858* (2013.01); *C12Q 1/6876* (2013.01)

(58) Field of Classification Search
CPC ........................ C12Q 1/6827; C12Q 2527/107
See application file for complete search history.

(56) References Cited

U.S. PATENT DOCUMENTS

2010/0216123 A1* 8/2010 Hirai .................... C12Q 1/6827 435/6.1
2020/0056228 A1* 2/2020 Michiyuki ............. G01N 21/78

FOREIGN PATENT DOCUMENTS

| EP | 2 031 074 A1 | 3/2009 |
| EP | 2 520 663 A1 | 11/2012 |
| EP | 2 761 021 A1 | 8/2014 |
| JP | 2007-117060 A | 5/2007 |
| JP | 5597939 B2 | 10/2014 |
| WO | 2008/018305 A1 | 2/2008 |

OTHER PUBLICATIONS

Crockett et al., Fluorescein-Labeled Oligonucleotides for Real-Time PCR: Using the Inherent Quenching of Deoxyguanosine Nucleotides. Analytical Biochemistry 290:89-97 (Year: 2001).*
Kamimura et al., Evaluation of Quenching Probe (QProbe)—PCR Assay for Quantification of the Koi Herpes Virus (KHV). Microbes and Environments. 22(3): 223-231 (Year: 2007).*
Kurata et al., Fluorescent quenching-based quantitative detection of specific DNA/RNA using a BODIPY® FL-labeled probe or primer. Nucleic Acids Research 29(6): e34 (Year: 2001).*
Meurs et al., A substitution mutation in the myosin binding protein Cgene in ragdoll hypertrophic cardiomyopathy. Genomics 90: 261-264 (Year: 2007).*
Torimura et al., Analytical Biochemistry 290:89-97 (Year: 2001).*
EP 1786551.8, dated May 4, 2020, Extended European Search Report.
PCT/JP2017/038458, dated Jan. 30, 2018, International Search Report and Written Opinion.

* cited by examiner

*Primary Examiner* — Ethan C Whisenant
(74) *Attorney, Agent, or Firm* — Brian S. Boyer; Syndicated Law, PC

(57) ABSTRACT

The present invention addresses the issue of providing a target base sequence detection method, etc., whereby a determination can be readily made regarding whether or not a target base sequence is present in a nucleic acid sample. A fluorescent-labeled detection probe and a competitive probe are added to a nucleic acid sample and caused to hybridize with the nucleic acid in the sample, the fluorescence intensity is measured while changing the temperature of the reaction sample, and first order differentiation is performed on a temperature-fluorescence intensity curve. The fluorescent-labeled detection probe and competitive probe base length, base sequence, and amount to be added to nucleic acid samples are determined such that the first order derivative curve for a control target reaction sample including a target base sequence has a peak but the first order derivative curve for a control non-target reaction sample including a non-target base sequence does not substantially have a peak, when: the fluorescent-labeled detection probe and the competitive probe are added to both the control target nucleic acid sample and the control non-target nucleic acid sample; the fluorescence intensity is measured while the temperature of both the obtained control target reaction sample and the control non-target reaction sample are changed; and first order differentiation is performed on a temperature-fluorescence intensity curve.

13 Claims, 8 Drawing Sheets
Specification includes a Sequence Listing.

[FIG.1]
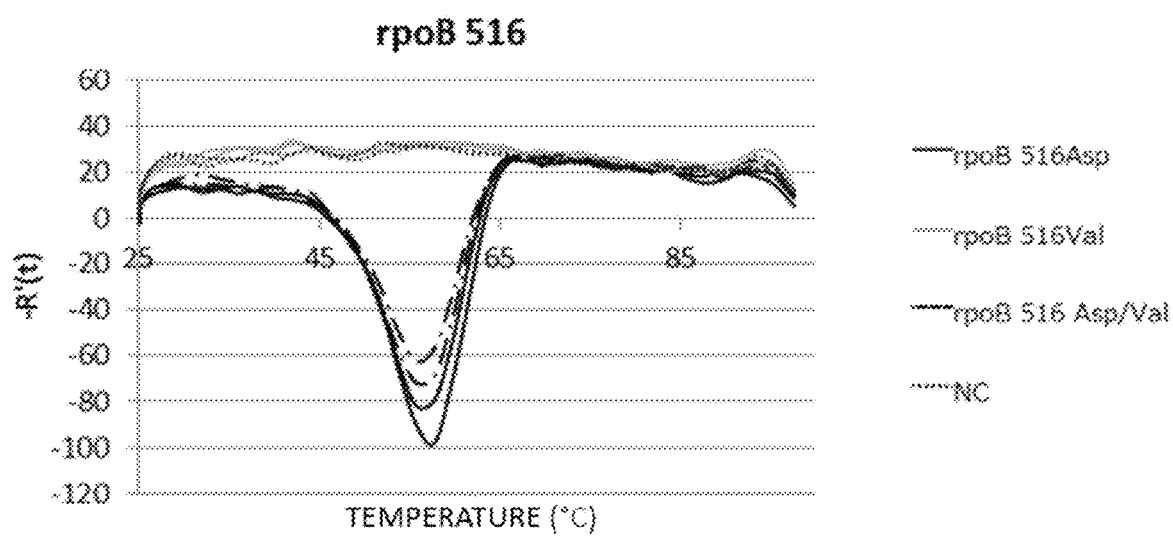

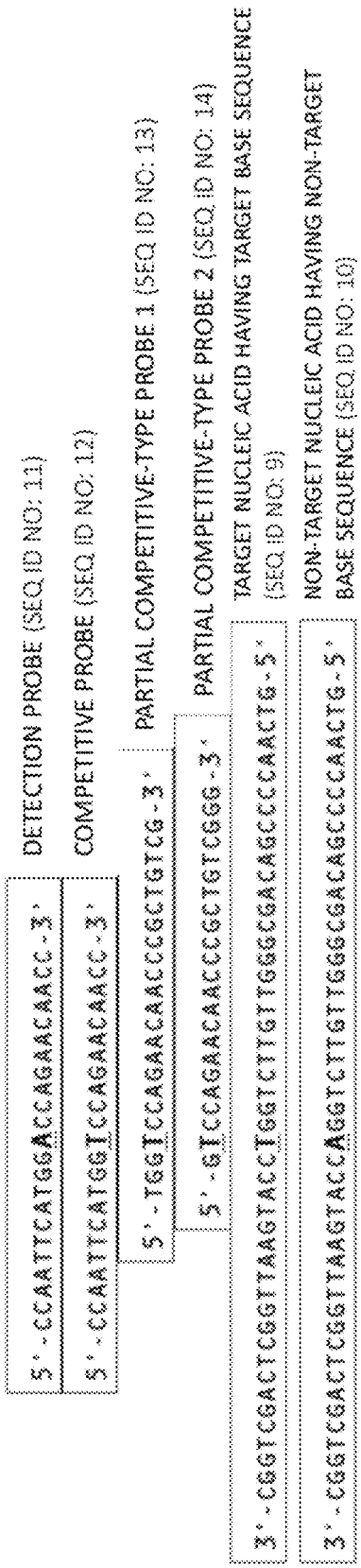

[FIG.3-1]
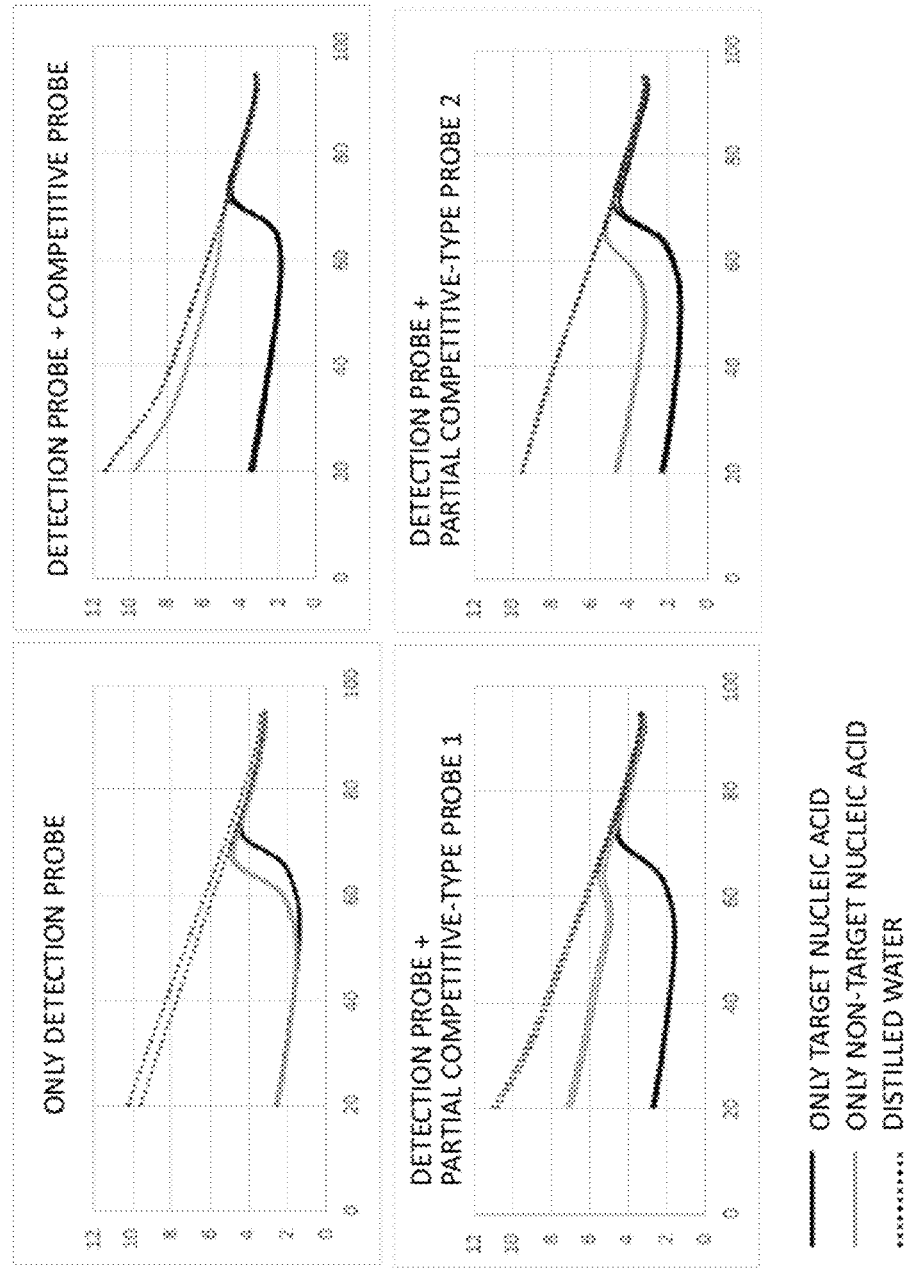

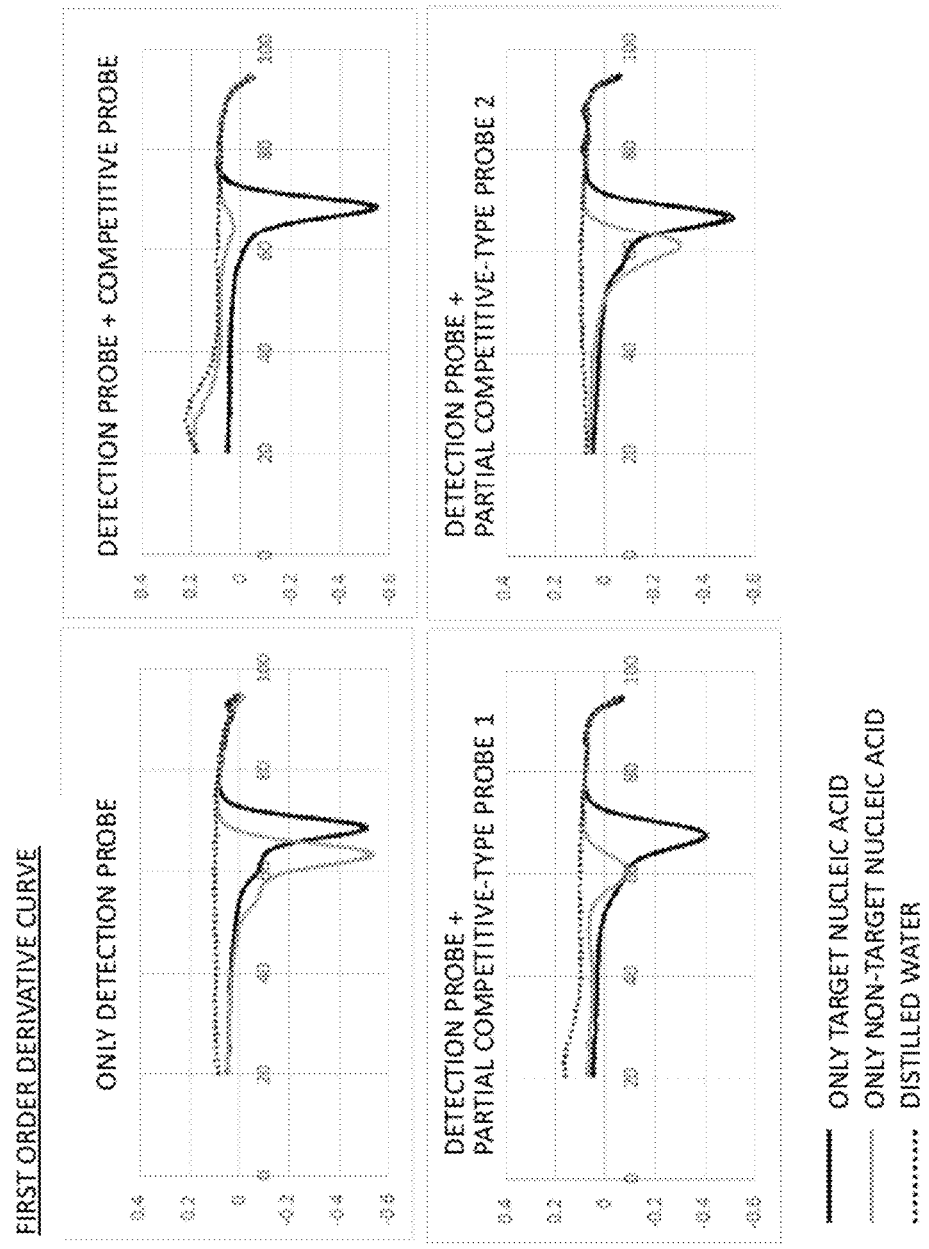
[FIG. 3-2]

[FIG.4-1]

SEQUENCES OF TARGET NUCLEIC ACID AND NON-TARGET NUCLEIC ACID (* WHEN T ALLELE WAS USED AS TARGET BASE SEQUENCE)

3'- CGGTCGACTCGGTTAAGTACCAGGTCTTGTTGGGCGACAGCCCCAACTG -5'  TARGET NUCLEIC ACID HAVING TARGET BASE SEQUENCE (SEQ ID NO: 10)

3'- CGGTCGACTCGGTTAAGTACCTGGTCTTGTTGGGCGACAGCCCCAACTG -5'  NON-TARGET NUCLEIC ACID HAVING NON-TARGET BASE SEQUENCE (SEQ ID NO: 9)

[FIG.4-2]

SEQUENCE AND Tm VALUE OF PROBE

| NAME | PERFECT MATCH | SEQUENCE | SEQ ID NO | OLIGO CONC. [μM] | Tm VALUE [°C] | | (FLUORESCENT-LABELED Tm [°C])—(COMPETITIVE Tm [°C]) | | | |
|---|---|---|---|---|---|---|---|---|---|---|
| | | | | | TO T ALLELE | TO A ALLELE | TO T ALLELE | QUEN-CHING | TO A ALLELE | QUEN-CHING |
| RS6184-Q-P-1 | T ALLELE | CCAATTCATGGCCAGAACAACC-BodipyFL | 15 | 0.04 | 50.8 | 47.9 | — | — | — | — |
| RS6184-Q-P-1 | A ALLELE | TTCATGGACCAGAAC-P | 16 | 1.2 | 35.3 | 45.7 | 10.6 | ○ | 9.9 | ○ |
| RS6184-Q-P-2 | A ALLELE | ATTCATGGACCAGAACA-P | 17 | 1.2 | 39.8 | 48.9 | 1.4 | ○ | -1.9 | ○ |
| RS6184-Q-P-3 | A ALLELE | AATTCATGGACCAGAACAA-P | 18 | 1.2 | 42.9 | 50.7 | 11.0 | ○ | -0.9 | ○ |
| RS6184-Q-P-4 | A ALLELE | CAATTCATGGACCAGAACAAA-P | 19 | 1.2 | 46.4 | 52.4 | 8.7 | ○ | -4.5 | ○ |
| RS6184-Q-P-5 | A ALLELE | CAATTCATGGACCAGAACAAAC-P | 20 | 1.2 | 47.1 | 53.9 | 8.6 | ○ | -6.9 | ○ |
| RS6184-Q-P-6 | A ALLELE | CCAATTCATGGACCAGAACAAAC-P | 21 | 1.2 | 49.7 | 55.0 | 4.9 | ○ | -9.1 | ○ |
| RS6184-Q-P-7 | A ALLELE | CCAATTCATGGACCAGAACAAACC-P | 22 | 1.2 | 53.1 | 58.0 | 1.8 | ○ | -10.1 | △ |
| RS6184-Q-P-8 | A ALLELE | AGCCAATTCATGGACCAGAACAACCCCG-P | 23 | 1.2 | 60 | 64.7 | -9.1 | △ | -16.8 | △ |
| RS6184-Q-P-9 | A ALLELE | CTGAGCCAATTCATGGACCAGAACAACCCCGG-P | 24 | 1.2 | 63.9 | 67.4 | -9.9 | × | -19.5 | × |
| RS6184-Q-P-10 | A ALLELE | CCTGAGCCAATTCATGGACCAGAACAACCCGGTGT-P | 25 | 1.2 | 67.1 | 70.5 | -13.2 | × | -22.8 | × |

Tm VALUE WAS CALCULATED USING Melcalc 99 free (http://www.melcalc.com/) UNDER SET CONDITION: Na eq. [mM] 50.

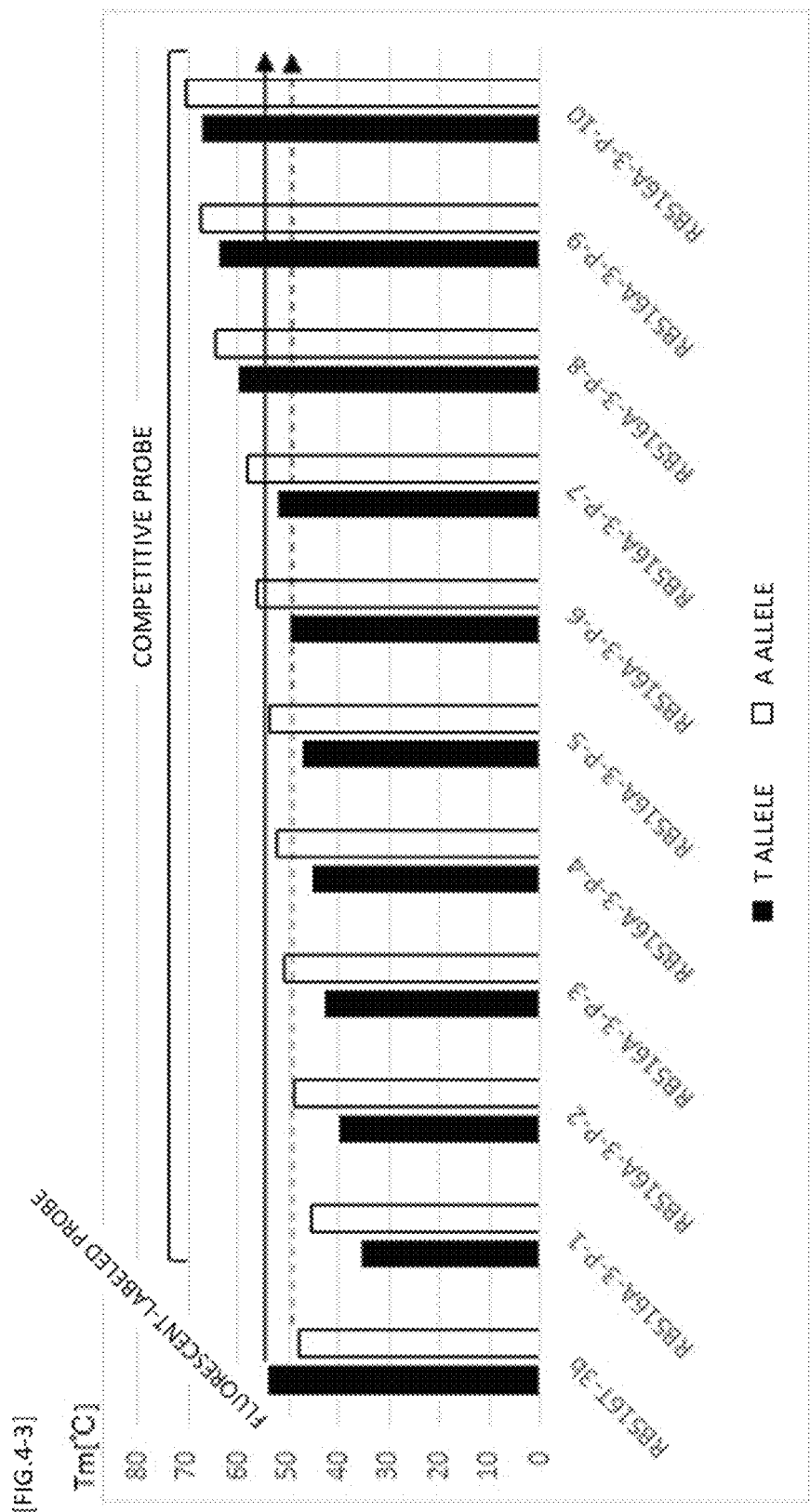

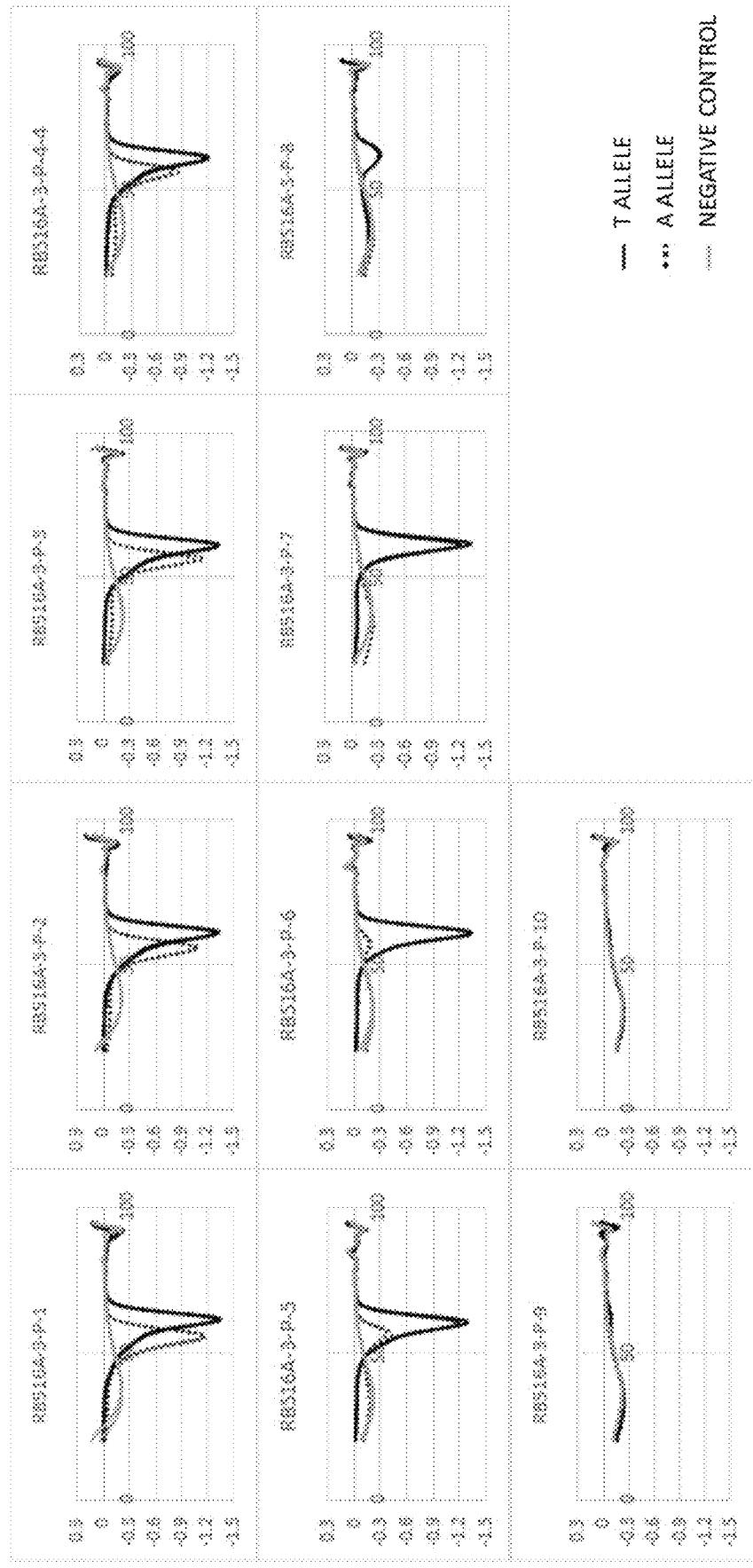
[FIG. 5]

METHOD FOR DETECTING A TARGET BASE SEQUENCE

CROSS-REFERENCE

[0001] This application is a national stage application of International application no. PCT/JP2017/038458, filed Oct. 25, 2017, which claims the benefit of Japanese application no. 2016-209929, filed on Oct. 26, 2016, each application of which is hereby incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jun. 2, 2021, is named PCT2842US_Revised2_Sequence_listing.bd and is 6087 bytes in size. The Sequence Listing is incorporated by reference in it's entirety in the specification.

TECHNICAL FIELD

The present invention relates to a method for detecting a target base sequence, more particularly relates to, for example, a method for detecting a target base sequence containing a single base mutation such as a single nucleotide polymorphism (SNP), a method for designing and a method for producing probes to be used in the method, and a kit including the probes.

BACKGROUND ART

A SNP is a mutation in which one nucleotide in a genomic sequence is replaced with a different nucleotide among individuals, and refers to a mutation present at a frequency exceeding 1% of the entire population of individuals. Among SNPs, there is a SNP that causes individual differences of various phenotypes such as traits, disease susceptibility, and drug responsiveness. For example, it is known that a human alcoholysis ability depends on a SNP of ALDH2 gene, and it is also known that a SNP in the CYP family associated with drug metabolism contributes to the effect of a drug on individual humans. Further, recently, a specific SNP has been reported as a biomarker for predicting a postoperative course for cancer or a therapeutic effect on cancer, and the usefulness of discrimination of SNPs is high. In addition, a technique for discriminating a difference of one base that is used for discrimination of SNPs can be effectively utilized also for discriminating a base sequence containing a mutation by a single base substitution (point mutation) as well as SNPs, and for example, it can also be applied to detection of a drug resistant pathogenic bacterium at an occurrence frequency less than 1%. Therefore, it is predicted that the demand for a technique capable of simply identifying a difference of a single base among base sequences will be increased.

As a simple discrimination method for SNPs, a probe detection method is known. The probe detection method is a method for discriminating base sequences based on a difference in Tm values by utilizing the fact that the Tm value of a perfectly matched double strand obtained by allowing a detection probe having a base sequence complementary to the base sequence of a detection target to hybridize therewith is higher than the Tm value of a double strand with a single base mismatch obtained by allowing the detection probe to hybridize with a nucleic acid of a base sequence having one different base from the base sequence of the detection target by about 5° C. The Tm value changes depending on the base composition of the base sequence of the detection target and conditions such as a salt concentration in a reaction sample, and such conditions become noise to make stable measurement results difficult to obtain in some cases. Therefore, measures for reducing such noise have been thought up.

For example, PTL 1 discloses a method in which a partial region of a "detection-type probe" is allowed to hybridize with a region containing a single base mutation site of a target nucleic acid at one of the 3'-end side and the 5'-end side, and allowing a partial region of a "partial competitive-type probe" having a base sequence that partially coincides with the detection-type probe other than the single base mutation site to hybridize with the other, and the rest of the regions of the detection-type probe and the partial competitive-type probe are allowed to compete for the region containing the single base mutation site, that is, a method in which both the detection-type probe and the partial competitive-type probe can hybridize with corresponding regions, respectively, in the target nucleic acid, but both these probes mutually compete for the region containing the single base mutation site. In this method, a mutation discriminating ability in the "region containing a single base mutation site" that is a competitive portion is enhanced, and also the stability of single base mismatch hybridization can be decreased, and therefore, the accuracy of discrimination based on a difference in Tm values from a case of perfect match can be enhanced.

PRIOR ART LITERATURES

Patent Literatures

[PATENT LITERATURE 1] PTL 1: JP Patent No. 5597939

SUMMARY OF THE INVENTION

Problem to be Solved by the Invention

However, there is no change in the method described in PTL 1, whether the base sequence contained in the nucleic acid sample is perfectly matched or has a single base mismatch with the base sequence of the detection probe is discriminated based on a difference in Tm values. The present inventors found that by the discrimination method based on a difference in Tm values, erroneous determination may be made depending on the experimental conditions such as a salt concentration or due to contaminants derived from a sample, formulation error, or the like, and there is room for improvement from the viewpoint of prevention of erroneous determination and simplification of determination of the presence or absence of a single base substitution.

As adopted also in PTL 1, in the measurement of the Tm value, e.g. a method for detecting quenching or emission of a fluorescent dye used for labeling a detection probe accompanying hybridization or dissociation of a nucleic acid and the detection probe such as a QP (Quenching Probe/Primer) method is used. In such a method, a fluorescence intensity is measured while changing the temperature of a reaction sample obtained by adding a detection probe to a nucleic acid sample, and a peak (maximum value) (corresponding to a temperature at which quenching or emission occurred) of a curve obtained by performing first order differentiation of a temperature-fluorescence intensity curve obtained from the measurement results is determined to be the Tm value. In the method for discriminating SNPs based on a difference in the Tm values, it is necessary to determine whether the measured Tm value is at a high temperature side or a low temperature side, and due to an error or the like, the determination may become difficult or erroneous determination may be made.

Further, for example, when a nucleic acid that is targeted for discrimination of SNPs is a heterozygote of two alleles of SNPs, a quenching or emission peak is observed at a temperature between a Tm value at a high temperature side and a Tm value at a low temperature side in some cases. In such a case, a difference between the Tm value of the measurement result and the Tm value at the high temperature side or the low temperature side becomes as small as, e.g. about 2° C., and discrimination is difficult.

Therefore, an object of the present invention is to provide a method for detecting a target base sequence capable of easily determining whether or not the target base sequence is present in a nucleic acid sample, a kit to be used in the method, and methods for designing and producing probes to be used in the method.

Means to Solve the Problem

In order to achieve the above object, the present inventors found while continuing intensive studies that a detection system capable of detecting only a target base sequence can be realized by inhibiting single base mismatch hybridization of a detection probe using a competitive probe that specifically hybridizes with a base sequence with a single base mismatch so as to prevent quenching or emission at a Tm value at a low temperature side from occurring. In addition, the present inventors found that when first order differentiation of a temperature-fluorescence intensity curve obtained for a reaction sample for hybridization of a detection probe and a nucleic acid is performed, a peak of a first order derivative curve generally appears accompanying quenching or emission at a temperature of a Tm value, however, by inhibiting single base mismatch hybridization of the detection probe so that such a peak does not appear, it can be clearly discriminated from a case where a peak appears by detection of a target base sequence, and thus completed the present invention.

That is, the present invention relates to the following matters.

[1] A method for detecting a target base sequence (A) containing a nucleotide with a mutated base from a nucleic acid sample, the method including the following steps:
  (1) adding a detection probe labeled with a fluorescent dye that can be used in a QP (Quenching Probe/Primer) method and a competitive probe to the nucleic acid sample, thereby obtaining a reaction sample, so that the fluorescent-labeled detection probe or the competitive probe hybridizes with a target nucleic acid having the target base sequence (A) in the reaction sample;
  (2) measuring a fluorescence intensity while changing the temperature of the reaction sample; and
  (3) performing first order differentiation of a temperature-fluorescence intensity curve obtained from the measurement results in (2), wherein
    (i) the base sequence of the fluorescent-labeled detection probe contains a base sequence (A') complementary to the target base sequence (A),
    (ii) the base sequence of the competitive probe contains a base sequence (B') complementary to a non-target base sequence (B) that is the same base sequence as the target base sequence (A) except that the nucleotide with a mutated base is replaced with a nucleotide with an unmutated base, and
    (iii) the base length, the base sequence, and the amount to be added to the nucleic acid sample of each of the fluorescent-labeled detection probe and the competitive probe are determined according to the following procedures:
      (a) adding the fluorescent-labeled detection probe and the competitive probe to each of a control target nucleic acid sample that contains the target nucleic acid, but does not substantially contain a non-target nucleic acid having the non-target base sequence (B) and a control non-target nucleic acid sample that does not substantially contain the target nucleic acid, but contains the non-target nucleic acid, thereby obtaining a control target reaction sample and a control non-target reaction sample;
      (b) measuring a fluorescence intensity while changing the temperature of each of the control reaction samples; and
      (c) performing first order differentiation of each of the temperature-fluorescence intensity curves obtained from the measurement results,
        so that a first order derivative curve for the control target reaction sample has a peak (maximum value), but a first order derivative curve for the control non-target reaction sample does not substantially have a peak.

[2] The method according to [1], further including the following step:
  (4) determining that the target base sequence (A) is present in the nucleic acid sample when the first order derivative curve obtained in (3) has a peak, wherein
    the nucleic acid sample may also contain a non-target nucleic acid other than the target nucleic acid.

[3] The method according to [1] or [2], wherein with respect to the non-target nucleic acid, the Tm value of the competitive probe is higher than the Tm value of the fluorescent-labeled detection probe by at least 5° C., and with respect to the target nucleic acid, the Tm value of the competitive probe is lower than the Tm value of the fluorescent-labeled detection probe.

[4] The method according to [1] or [2], wherein with respect to the non-target nucleic acid, the Tm value of the competitive probe is higher than the Tm value of the fluorescent-labeled detection probe by at least 10° C., and with respect to the target nucleic acid, the Tm value of the competitive probe is lower than the Tm value of the fluorescent-labeled detection probe.

[5] The method according to [1] or [2], wherein with respect to the non-target nucleic acid, the Tm value of the competitive probe is higher than the Tm value of the fluorescent-labeled detection probe by at least 10° C., and with respect to the target nucleic acid, the Tm value of the competitive probe does not exceed the Tm value of the fluorescent-labeled detection probe+5° C.

[6] The method according to [1] or [2], wherein with respect to the non-target nucleic acid, the Tm value of the competitive probe is higher than the Tm value of the fluorescent-labeled detection probe by at least 15° C., and with respect to the target nucleic acid, the Tm value of the competitive probe does not exceed the Tm value of the fluorescent-labeled detection probe+5° C.

[7] The method according to [1] or [2], wherein with respect to the non-target nucleic acid, the Tm value of the competitive probe is higher than the Tm value of the fluorescent-labeled detection probe by at least 15° C., and with respect to the target nucleic acid, the Tm value of the competitive probe is lower than the Tm value of the fluorescent-labeled detection probe.

[8] The method according to any one of [1] to [7], wherein (I) a region that hybridizes with the fluorescent-labeled detection probe in the target nucleic acid contains a region that hybridizes with the competitive probe; (II) a region that hybridizes with the competitive probe in the target nucleic acid contains a region that hybridizes with the fluorescent-labeled detection probe; or (III) a region that hybridizes with the competitive probe in the target nucleic acid coincides with a region that hybridizes with the fluorescent-labeled detection probe.

[9] The method according to any one of [1] to [8], wherein the amount to be added of the competitive probe to the nucleic acid sample is at least 10 times (molar ratio) the amount to be added of the fluorescent-labeled detection probe.

[10] The method according to any one of [1] to [9], wherein the amount to be added of the competitive probe to the nucleic acid sample is at least 20 times (molar ratio) the amount to be added of the fluorescent-labeled detection probe.

[11] The method according to any one of [1] to [10], wherein the fluorescent dye that can be used in the QP (Quenching Probe/Primer) method is at least one type of fluorescent dye selected from the group consisting of TAMRA™ (tetramethyl rhodamine), BODIPY® FL (4,4-difluoro-5,7-dimethyl-4-bora-3a,4a-diaza-s-indacen-3-propionic acid), PACIFIC BLUE™ (3-carboxy-6,8-difluoro-7-hydroxycoumarin), and CR6G® (carboxy rhodamine 6G).

[12] The method according to any one of [1] to [11], wherein the nucleic acid sample is derived from a living body.

[13] The method according to any one of [1] to [12], wherein the nucleotide with a mutated base is a DNA containing a single base substitution mutation.

[14] A method for designing a fluorescent-labeled detection probe and a competitive probe that can be used in the method according to any one of [1] to [13], the method including:
(1') determining the base length and the base sequence of each of the fluorescent-labeled detection probe and the competitive probe according to (a) to (c) so that a first order derivative curve for a control target reaction sample has a peak (maximum value), but a first order derivative curve for a control non-target reaction sample does not substantially have a peak.

[15] A method for producing a fluorescent-labeled detection probe and a competitive probe that can be used in the method according to any one of [1] to [13], the method including:
(1") synthesizing oligonucleotides having a base length and a base sequence of each designed by following the method according to [14]; and
(2") labeling the oligonucleotide of the fluorescent-labeled detection probe with a fluorescent dye that can be used in the QP method.

[16] A kit to be used in the method according to any one of [1] to [13], including a fluorescent-labeled detection probe, a competitive probe, and an instruction manual.

Effects by the Invention

According to the present invention, in a case where a non-target base sequence with a single base mismatch whose detection is desired to be avoided, a competitive probe specific to this non-target base sequence is allowed to hybridize therewith so as to prevent single base mismatch hybridization of a fluorescent-labeled detection probe from occurring, whereby a quenching or emission peak can be made to appear only when a target base sequence is detected in a measurement result of a temperature-fluorescence intensity. Therefore, unlike a discrimination method utilizing a difference in Tm values, the presence or absence of the target base sequence is found based on the presence or absence of the quenching or emission peak, and thus, whether or not the target base sequence is present in a nucleic acid sample can be made easily determinable without being affected by conditions such as a salt concentration that would affect the Tm values (high robustness).

BRIEF DESCRIPTION OF DRAWINGS

FIG. 1 shows first order derivative curves (thermal dissociation curves) of temperature-fluorescence intensity curves measured by adding a detection probe and a competitive probe for detecting a wild type (rpoB 516Asp) to a nucleic acid sample containing a point mutation (a wild type, a mutant type, and a wild-type/mutant-type heterozygote) at the 516th codon of a rpoB gene in Example 1.

FIG. 2 shows the base sequences of a target nucleic acid and a non-target nucleic acid amplified from a rpoB gene and a fluorescent-labeled detection probe and various competitive probes designed for detecting the target nucleic acid in Example 2.

FIG. 3-1 shows temperature-fluorescence intensity curves obtained for respective reaction samples in Example 2.

FIG. 3-2 shows curves obtained by performing first order differentiation of the temperature-fluorescence intensity curves obtained in Example 2.

FIG. 4-1 shows the base sequences of a target nucleic acid and a non-target nucleic acid amplified from a rpoB gene in Example 3.

FIG. 4-2 shows the base sequences of a fluorescent-labeled detection probe and various competitive probes designed for detecting the target nucleic acid, Tm values at which each probe hybridizes with each of the target nucleic acid and the non-target nucleic acid, and a value obtained by subtracting the Tm value of each competitive probe from the Tm value of the fluorescent-labeled detection probe with respect to each of the target nucleic acid and the non-target nucleic acid, and the presence or absence of a quenching peak in the first order derivative curve of the temperature-fluorescence intensity curve in each case in Example 3.

FIG. 4-3 shows Tm values at which the fluorescent-labeled detection probe and various competitive probes designed for detecting the target nucleic acid hybridize with each of the target nucleic acid and the non-target nucleic acid in Example 3.

FIG. 5 shows curves obtained by performing first order differentiation of the temperature-fluorescence intensity curves obtained in Example 3.

MODES FOR PRACTICING THE INVENTION

Hereinafter, the present invention will be described in detail.

Incidentally, in this description, the term SNP is used in the same meaning as SNPs in this technical field. Further, in this description, with respect to a matter described using the term SNP, a similar explanation is basically possible even if "SNP" is replaced with "DNA containing a single base substitution mutation". That is, in the following description, the SNP is an example of a detection target, and the present invention can be widely applied to a technique for detecting a DNA containing a single base substitution mutation.

Unless otherwise indicated herein, scientific and technical terms used in connection with the present invention shall have the meaning commonly understood by a person skilled in the art. In general, the terms and techniques thereof used in connection with molecular biology, microbiology, and gene, protein, and nucleic acid chemistry described herein are well known in this technical field and shall be those commonly used. All patents, applications, and other publications cited herein are incorporated herein by reference in their entirety.

<Detection Method>

The detection method according to the present invention is a method for detecting a target base sequence (A) containing a nucleotide with a mutated base from a nucleic acid sample including at least the following steps (1) to (3):

(1) adding a fluorescent-labeled detection probe and a competitive probe to the nucleic acid sample, thereby obtaining a reaction sample, so that the fluorescent-labeled detection probe or the competitive probe hybridizes with a target nucleic acid having the target base sequence in the reaction sample;

(2) measuring a fluorescence intensity while changing the temperature of the reaction sample; and (3) performing first order differentiation of a temperature-fluorescence intensity curve obtained from the measurement results in (2).

In this description, the "detecting a target base sequence" refers to discriminating whether or not a base sequence of a nucleic acid contained in a nucleic acid sample contains the same base sequence as the target base sequence.

The nucleic acid is not particularly limited as long as it is a DNA or an RNA, and may be a natural one or a synthesized one. Examples of the natural nucleic acid include genomic DNAs, mRNAs, rRNAs, and heteronuclear (hn) RNAs collected from an organism. Further, examples of the synthesized nucleic acid include DNAs synthesized by a known chemical synthetic method such as a β-cyanoethyl phosphoramidite method or a DNA solid-phase synthetic method, nucleic acids synthesized by a known nucleic acid synthetic method such as PCR, and cDNAs synthesized by reverse transcription.

In this description, a nucleic acid having a base sequence containing a target base sequence is referred to as "target nucleic acid".

The "nucleic acid sample" is not particularly limited as long as it is a sample containing a nucleic acid, and is preferably a sample obtained by extracting a nucleic acid from an animal, a plant, a microorganism, cultured cells, or the like. The extraction of a nucleic acid from an animal or the like can be performed by, e.g. a known method such as a phenol/chloroform method. The nucleic acid sample may be a sample derived from a living body. Here, the description that the nucleic acid sample is "derived from a living body" is not limited to the meaning that the nucleic acid sample is a sample collected from a living body itself, but the nucleic acid sample may be any as long as it is a material starting from a sample collected from a living body, and for example, a case where it is subjected to a genetic engineering operation such as amplification, cloning, or incorporation in another base sequence after extraction of a nucleic acid is also included. For example, a nucleic acid after amplification, a cloned nucleic acid, and the like are also included in the "nucleic acid sample derived from a living body". With respect to the nucleic acid sample derived from a living body, by applying the method of the present invention, it can be utilized for a genetic diagnosis of the living body.

Incidentally, when the nucleic acid contained in the nucleic acid sample is a double-stranded nucleic acid, it is preferred to dissociate it into a single-stranded nucleic acid in advance. By using a single-stranded nucleic acid, in the below-mentioned step (1), a detection probe or a competitive probe can be made to hybridize with the single-stranded nucleic acid. The dissociation of the extracted double-stranded nucleic acid into single strands can be performed by a known method such as applying heat energy.

The "hybridization" refers to that single-stranded nucleic acids (e.g., a DNA that is a detection target dissociated into a single strand by a heat treatment and a probe) are annealed into a double strand by forming complementary base pairs. In this description, in the "hybridization", a case where a base sequence perfectly complementary to one base sequence hybridizes therewith, and a case where even if there is a portion (mismatch portion) in which, for example, one to several base pairs cannot form a complementary base pair between one base sequence and the other base sequence, portions having complementation form base pairs, whereby the sequences hybridize with each other as a whole are included. In this description, a case where a base sequence perfectly complementary to one base sequence hybridizes therewith is sometimes expressed as "perfect match hybridization" or "specifically hybridize", and a case where a mismatch is contained is sometimes expressed as "mismatch hybridization" or "nonspecifically hybridize".

In this description, examples of a different site of a base of the "nucleotide with a mutated base" and the "nucleotide with an unmutated base" include mutation sites due to a SNP, an insertion mutation, a deletion mutation, or a repetitive sequence mutation.

Typically, such a different site is a mutation site in a SNP, and the "nucleotide with a mutated base" and the "nucleotide with an unmutated base" are each one nucleotide. However, for example, when the base mutation is a single base deletion mutation, the present invention can also be applied by regarding two consecutive bases sandwiching a deletion site as the "nucleotide with a mutated base", and regarding three consecutive bases containing no deletion as the "nucleotide with an unmutated base". Further, for example, when the base mutation is a single base insertion mutation, the present invention can also be applied by regarding a total of three bases of the inserted nucleotide and the consecutive nucleotides on both sides thereof as the "nucleotide with a mutated base", and regarding two consecutive bases containing no insertion as the "nucleotide with an unmutated base". The number of deleted bases or the number of inserted bases may be 2 or more bases. That is, the description that "the nucleotide with a mutated base is replaced with a nucleotide with an unmutated base" in the claims appended to this application also includes a case where the "nucleotide with a mutated base" and the "nucleotide with an unmutated base" are each several consecutive nucleotides.

In the present invention, a relationship between the "nucleotide with a mutated base" and the "nucleotide with an unmutated base" can also be said to be a relative relationship of mutually different bases of a wild type and a mutant type in alleles such as SNPs. Therefore, typically, the "target base sequence containing a nucleotide with a mutated base" is a mutant-type base sequence, and the "non-target base sequence" containing a "nucleotide with an unmutated base" is a wild-type base sequence, however, on the contrary, the "target base sequence containing a nucleotide with a mutated base" may be regarded as a wild-type base sequence, and at the same time, the "non-target base sequence" containing a "nucleotide with an unmutated base" may be regarded as a mutant-type base sequence. The latter case will be described in the below-mentioned Examples 1 and 2. That is, the "mutated" in the term of "nucleotide with a mutated base" and the "unmutated" do not necessarily mean whether or not the nucleotide is a mutant type, but mean whether or not the nucleotide has a different base based on the base at a SNP site (a site where a mutation can occur by a single base substitution according to the detection) in the non-target base sequence that is not a detection target in this method.

In this specification, the "target base sequence" refers to a partial sequence with a given length containing a nucleotide with a mutated base in a base sequence of a nucleic acid (target nucleic acid) containing a nucleotide with a mutated base of interest. The length of the target base sequence is not particularly limited as long as a probe containing a base sequence complementary to the partial sequence and having the same length can specifically hybridize therewith under stringent conditions. Further, the length of the target base sequence can be appropriately determined in consideration of the type of the target base sequence, the base sequences of the below-mentioned detection probe and competitive probe, and the like.

In this description, the "non-target base sequence" refers to a base sequence that is the same as the target base sequence except that a nucleotide with a mutated base is replaced with a nucleotide with an unmutated base. Such a non-target base sequence is not a detection target, but is similar to the target base sequence that is a detection target, and therefore can nonspecifically hybridize with the detection probe having a base sequence complementary to the target base sequence. Due to this, in a conventional probe method, other than the target base sequence, the non-target base sequence is also sometimes detected by hybridization with the detection probe, and in a case where the detected base sequence is the non-target base sequence, thermal stability (Tm value) of hybridization is lower than in a case of the target base sequence, and therefore, discrimination is made based on this (specifically, see "only detection probe" in the following Example 2).

In this description, a nucleic acid having a base sequence containing this non-target base sequence is referred to as "non-target nucleic acid".

In this description, the "detection probe" and the "competitive probe" are each a probe obtained by connecting one or more members selected from the group consisting of a nucleotide, a nucleotide analog, and a modified body thereof through a phosphodiester bond.

Here, the nucleotide analog is an unnatural nucleotide, and is referred to as a substance having a function similar to that of a deoxyribonucleotide (DNA) or a ribonucleotide (RNA) that is a natural nucleotide. That is, the nucleotide analog can form a strand through a phosphodiester bond in the same manner as a nucleotide, and also a primer or a probe formed using the nucleotide analog can be used in PCR or hybridization in the same manner as a primer or a probe formed using only a nucleotide. Examples of such a nucleotide analog include PNAs (polyamide nucleotide derivatives), LNAs (BNAs), ENAs (2'-O,4'-C-Ethylene-bridged nucleic acids), and complexes thereof. Here, the PNA is a substance in which a main chain composed of phosphoric acid and a pentose of a DNA or an RNA is substituted with a polyamide chain. Further, the LNA (BNA) is a compound having two cyclic structures in which an oxygen atom at the 2'-position and a carbon atom at the 4'-position of a ribonucleoside are bound to each other through methylene.

Here, examples of the modified body include modified deoxyribonucleotides, modified ribonucleotides, modified phosphate-sugar-backbone oligonucleotides, modified PNAs, modified LNAs (BNAs), and modified ENAs. Here, a substance to be used for modifying a nucleotide or a nucleotide analog is not particularly limited as long as the effects of the present invention are not impaired, and a substance generally used for modifying a nucleotide or the like can be used. Examples of the modified nucleotide and the modified nucleotide analog include nucleotides and the like modified with a functional group such as an amino group, a carboxyvinyl group, a phosphate group, or a methyl group, nucleotides and the like modified by 2-O-methylation with a methyl group, nucleotides and the like modified by phosphorothioate, and nucleotides and the like modified with a labeling molecule such as the below-mentioned fluorescent dye.

The detection probe is labeled with a fluorescent dye that can be used in a QP (Quenching Probe/Primer) method. The QP method is a detection method utilizing the phenomenon that fluorescence is quenched by spatial proximity of a guanine base to a certain type of fluorescent dye. By labeling the detection probe with a fluorescent dye that is quenched by proximity to a guanine base, the presence or absence of proximity of the detection probe to the target nucleic acid (containing a guanine base) can be detected. Specifically, in the target nucleic acid, the target base sequence is set so as to have a guanine base inside, and also the detection probe is designed in advance so as to have a cytosine base labeled with a fluorescent dye at a site complementary to the guanine base of the target nucleic acid. When the target nucleic acid and the detection probe hybridize with each other, proximity of the fluorescent dye of the labeled detection probe to the guanine base in the target nucleic acid occurs, and the fluorescent dye is quenched.

Examples of the fluorescent dye that can be used in the QP method include TAMRA™ (manufactured by Invitrogen, Inc.), BODIPY® FL (manufactured by Invitrogen, Inc.), PACIFIC BLUE™ (manufactured by Invitrogen, Inc.), and CR6G® (manufactured by Invitrogen, Inc.). The labeling of the detection probe with each fluorescent dye can be performed by a generally used method such as an organic synthetic method.

Hereinafter, the detection probe is also referred to as "fluorescent-labeled detection probe".

The base sequence of the fluorescent-labeled detection probe contains a base sequence (A') complementary to the target base sequence (A). The base sequence of the competitive probe contains a base sequence (B') complementary to the non-target base sequence (that is, a base sequence that is the same as the target base sequence except that a nucleotide with a mutated base is replaced with a nucleotide with an unmutated base) (B). The "base sequence of the probe" refers to the full-length base sequence of a region that hybridizes with the nucleic acid of the probe. Incidentally, in this description, the "complementary" in the phrase of "a base sequence (A') complementary to the target base sequence (A)" means that the base sequences (A) and (A') are in a perfectly complementary relationship, and all the base pairs of a double-stranded portion formed by the base sequences (A) and (A') are complementary to each other. The "complementary" in the phrase of "a base sequence (B') complementary to the non-target base sequence (B)" also means that the base sequences (B) and (B') are in a perfectly complementary relationship similarly.

The condition that the "base sequence of the fluorescent-labeled detection probe" "contains a base sequence complementary to the target base sequence" includes a case where the base sequence (A') of the fluorescent-labeled detection probe is complementary to the target base sequence (A) and a case where the base sequence (A') of the fluorescent-labeled detection probe is complementary to the base sequence of a region that contains the target base sequence (A) in the target nucleic acid and is longer than the target base sequence (A).

The condition that the "base sequence of the competitive probe" "contains a base sequence complementary to the non-target base sequence" includes a case where the base sequence (B') of the competitive probe is complementary to the non-target base sequence (B) and a case where the base sequence (B') of the competitive probe is complementary to the base sequence of a region that contains the non-target base sequence (B) in the non-target nucleic acid and is longer than the non-target base sequence (B).

The respective steps included in the detection method of the present invention will be described.

First, in the step (1), the fluorescent-labeled detection probe or the competitive probe is allowed to hybridize with a target nucleic acid having a target base sequence in a reaction sample. The base length, the base sequence, and the amount to be added to the nucleic acid sample of each of the fluorescent-labeled detection probe and the competitive probe are determined so as to satisfy predetermined conditions, however, the conditions will be described later. The reaction conditions for hybridization of the target nucleic acid with the fluorescent-labeled detection probe or the competitive probe are not particularly limited, and the reaction can be performed under the conditions of normal temperature, pH, salt concentration, buffer solution, etc. in consideration of the Tm values of the fluorescent-labeled detection probe or the competitive probe.

Here, the Tm value is a temperature when 50% of oligonucleotides are dissociated from the complementary strand thereto, and is an index of thermal stability of a double strand when a probe is allowed to hybridize with a nucleic acid. As a calculation method for the Tm value, a usual method can be used, and for example, in a case of a probe of 17 to 25 bases, it can be roughly calculated according to the following formula (Wallace formula).

$Tm=2\times$(the number of $As$ in the sequence+the number of $Ts$ in the sequence)+$4\times$(the number of $Gs$ in the sequence+the number of $Cs$ in the sequence)

Further, in order to ensure more accuracy, the Tm value can be calculated according to, e.g. a conventionally known MELTCALC software (http:/www.meltcalc.com/) or the like, and also can be determined by a nearest neighbor method.

The hybridization reaction is preferably performed in a reaction solution containing a salt having a buffering action. The pH of the reaction solution is preferably within a range of 6.5 to 8.5, more preferably within a range of 6.7 to 7.7, and the salt concentration in the reaction solution is preferably within a range of 5 to 250 mM, more preferably within a range of 10 to 100 mM. Examples of the salt having a buffering action include cacodylates, phosphates, and Tris salts. Further, the reaction solution preferably contains a salt of an alkali metal and/or an alkaline earth metal, and more preferably contains sodium chloride and/or magnesium chloride.

With the target nucleic acid, the fluorescent-labeled detection probe containing a base sequence complementary to the target base sequence preferentially hybridizes. By hybridization of the fluorescent-labeled detection probe with the nucleic acid, fluorescence is quenched. There is also a case where the competitive probe hybridizes to some extent with the target nucleic acid. The ratio of hybridization of the competitive probe with the target nucleic acid is such a degree that the ratio of hybridization of the fluorescent-labeled detection probe with the target nucleic acid is sufficiently high and the detection thereof is not substantially hindered.

Incidentally, when the non-target nucleic acid having the non-target base sequence is present in the nucleic acid sample, in this step, the competitive probe preferentially hybridizes with the non-target nucleic acid. As a result, mismatch hybridization of the fluorescent-labeled detection probe with the non-target nucleic acid is mostly inhibited, and quenching or emission due to the mismatch hybridization is not substantially detected.

Therefore, when quenching or emission of the fluorescent dye used for labeling the fluorescent-labeled detection probe is detected, it is found that the target nucleic acid having the target base sequence complementary to the base sequence of the fluorescent-labeled detection probe is present in the nucleic acid sample. Further, when quenching or emission is not detected, it is found that the target base sequence complementary to the base sequence of the fluorescent-labeled detection probe is not present in the nucleic acid sample.

Quenching or emission of the fluorescent dye used for labeling the fluorescent-labeled detection probe can be detected by performing the steps (2) and (3). In the step (2), by measuring a fluorescence intensity while changing the temperature of the reaction sample, a temperature-fluorescence intensity curve that shows a change in fluorescence intensity is obtained. As a method for measuring the fluorescence intensity while changing the temperature of the reaction sample, e.g., a commercially available real-time PCR device (ABI Prism® 7900HT, ABI Prism 7700 (Applied Biosystems), iCycler iQ™ Real-Time PCR Detection System (BIO-RAD), MX3000p, MX3005p (Agilent technologies), or the like can be utilized, and specifically, a melting curve analysis function similar to a fluorescence analysis in real-time PCR can be utilized. In the step (3), by performing first order differentiation of the temperature-fluorescence intensity curve obtained in the step (2), irregularities of the temperature-fluorescence intensity curve can be sensitively observed. The first order differentiation of the temperature-fluorescence intensity curve can be easily performed using a dedicated software for the above-mentioned real-time PCR device. When quenching or emission due to hybridization or dissociation of the fluorescent-labeled detection probe occurs, the ratio of the change in the fluorescence intensity is increased at the Tm value, and therefore, a peak (maximum value) appears in the result of the first order differentiation. Incidentally, in this description, the "peak (maximum value)" is not limited to the maximum value at the plus side, but also represents the maximum value at the minus side (see, Examples). In particular, in a case where a fluorescent-labeled detection probe labeled with a fluorescent dye such as TAMRA™ or BODIPY® FL that is quenched by proximity to a nucleic acid is used, when the temperature is decreased to the Tm value or lower, the fluorescence of the fluorescent-labeled detection probe is quenched due to hybridization, and therefore, a peak appears at the minus side, however, in this description, this is sometimes called "quenching peak".

Here, in the present invention, when a non-target nucleic acid that can hybridize with the fluorescent-labeled detection probe with a single base mismatch is contained in the reaction sample, the conditions for the fluorescent-labeled detection probe and the competitive probe are set so that a peak due to mismatch hybridization does not appear in the result of first order differentiation by inhibiting hybridization of the fluorescent-labeled detection probe with the non-target nucleic acid by the competitive probe.

The base length, the base sequence, and the amount to be added to the nucleic acid sample of each of the fluorescent-labeled detection probe and the competitive probe are determined according to the following procedures:

(a) adding the fluorescent-labeled detection probe and the competitive probe to each of a control target nucleic acid sample that contains the target nucleic acid, but does not substantially contain the non-target nucleic acid having the non-target base sequence (B) and a control non-target nucleic acid sample that does not substantially contain the target nucleic acid, but contains the non-target nucleic acid, thereby obtaining a control target reaction sample and a control non-target reaction sample;

(b) measuring a fluorescence intensity while changing the temperature of each of the control reaction samples; and (c) performing first order differentiation of each of the temperature-fluorescence intensity curves obtained from the measurement results, so as to satisfy functional conditions that a first order derivative curve for the control target reaction sample has a peak (maximum value), but a first order derivative curve for the control non-target reaction sample does not substantially have a peak.

The description that not "substantially" contain the non-target nucleic acid or the target nucleic acid means not only a case where the non-target nucleic acid or the target nucleic acid is not at all contained in the sample, but also a case where the non-target nucleic acid or the target nucleic acid is contained in such a small amount that it is not detected. The conditions that "a first order derivative curve for the control non-target reaction sample does not substantially have a peak" may, for example, in a precise sense, include a case where even if the first order derivative curve for the control non-target reaction sample has a peak, the intensity of the peak (the maximum deflection width of the fluorescence intensity) becomes significantly weak (flattened) as compared with the intensity of the peak of the first order derivative curve of the control target reaction sample, and the peak does not have the shape of a peak as in the first order derivative curve of the control target reaction sample.

The conditions for the base length, the base sequence, and the amount to be added to the nucleic acid sample of each of the fluorescent-labeled detection probe and the competitive probe can be experimentally determined according to the above-mentioned procedures (a) to (c) without imposing an excess burden on a person skilled in the art, and practically, it is only necessary to determine at least two correlated elements of the Tm value of each probe and the amount (molar ratio) to be added of each probe. For example, as shown below, an example of favorable conditions for the base length, the base sequence, and the amount to be added to the nucleic acid sample of each of the fluorescent-labeled detection probe and the competitive probe having a high possibility of satisfying the above-mentioned functional conditions has been found by the present inventors. A person skilled in the art can also determine the base length, the base sequence, and the amount to be added to the nucleic acid sample of each of the fluorescent-labeled detection probe and the competitive probe so as to satisfy the above-mentioned conditions based on the example.

The present inventors found that, for example, as the conditions for the base length and the base sequence of each of the fluorescent-labeled detection probe and the competitive probe, it is preferred that with respect to the non-target nucleic acid, the Tm value of the competitive probe is higher than the Tm value of the fluorescent-labeled detection probe by at least 5° C., preferably at least 6° C., 7° C., 8° C., 9° C., 10° C., 11° C., 12° C., 13° C., 14° C., 15° C., 16° C., 17° C., 18° C., 19° C., or 20° C., and also with respect to the target nucleic acid, the Tm value of the competitive probe is lower than the Tm value of the fluorescent-labeled detection probe, preferably lower by at least 1° C., 2° C., 3° C., 4° C., 5° C., 6° C., 7° C., 8° C., 9° C., or 10° C.

Although it depends on the molar ratio of the fluorescent-labeled detection probe/the competitive probe, when a difference between the Tm value of the competitive probe and the Tm value of the fluorescent-labeled detection probe with respect to the non-target nucleic acid is at least 5° C., there is a tendency that a peak due to mismatch hybridization of the fluorescent-labeled detection probe with the non-target nucleic acid is likely to be suppressed. Further, when with respect to the target nucleic acid, the Tm value of the competitive probe is lower than the Tm value of the fluorescent-labeled detection probe, there is a tendency that hybridization of the fluorescent-labeled detection probe with the target nucleic acid is more likely to occur, and when the target nucleic acid is detected, a peak of the first order derivative curve becomes sharper.

Incidentally, a difference between the Tm value of the competitive probe and the Tm value of the fluorescent-labeled detection probe with respect to the non-target nucleic acid, and a difference between the Tm value of the competitive probe and the Tm value of the fluorescent-labeled detection probe with respect to the target nucleic acid change in a correlated manner and cannot be independently set. Therefore, depending on the sequence to be targeted, there may be a case where the above-mentioned favorable combination of the Tm value conditions cannot be satisfied. For example, there may be a case where when with respect to the non-target nucleic acid, the Tm value of the competitive probe is higher than the Tm value of the fluorescent-labeled detection probe by at least 10° C., 11° C., 12° C., 13° C., 14° C., 15° C., 16° C., 17° C., 18° C., 19° C., or 20° C., with respect to the target nucleic acid, the Tm value of the competitive probe does not become lower than the Tm value of the fluorescent-labeled detection probe. If with respect to the target nucleic acid, the Tm value of the competitive probe is higher than the Tm value of the fluorescent-labeled detection probe, hybridization of the fluorescent-labeled detection probe with the target nucleic acid is likely to be prevented by the competitive probe, and as a result, a tendency that a peak of the first order derivative curve when the target nucleic acid is detected is attenuated occurs. However, also in such a case, if a peak due to mismatch hybridization of the fluorescent-labeled detection probe with the non-target nucleic acid is sufficiently suppressed (flattened) and the presence or absence of the peak can be visually determined, the effects of the present invention is achieved, and therefore, such a case can be said to be favorable. For example, it has been found that a case where with respect to the non-target nucleic acid, the Tm value of the competitive probe is higher than the Tm value of the fluorescent-labeled detection probe by at least 10° C., preferably 11° C., 12° C., 13° C., or 14° C., more preferably 15° C., 16° C., 17° C., 18° C., 19° C., or 20° C., and with respect to the target nucleic acid, the Tm value of the competitive probe does not exceed the Tm value of the fluorescent-labeled probe+5° C., preferably the Tm value of the fluorescent-labeled probe+4° C., the Tm value of the fluorescent-labeled probe+3° C., the Tm value of the fluorescent-labeled probe+2° C., the Tm value of the fluorescent-labeled probe+1° C., or does not exceed the Tm value of the fluorescent-labeled probe can also be favorable (specifically, see an example using "RB516A-3-P-8" as the competitive probe in the following Example 3).

Further, as the conditions for the amount to be added to the nucleic acid sample of each of the fluorescent-labeled detection probe and the competitive probe, conditions in which the amount to be added of the competitive probe is at least one time (that is, 1:1) at a molar ratio, preferably at least 2 to 9 times (molar ratio), more preferably at least 10 times (molar ratio), further more preferably at least 20 times, 30 times, 40 times, 50 times, 60 times, 70 times, 80 times, 90 times, 100 times, 150 times, 200 times, 250 times, 300 times, 400 times, 500 times, or 1000 times (molar ratio) the amount to be added of the fluorescent-labeled detection probe are exemplified. Although it depends on the difference in Tm value between the competitive probe and the fluorescent-labeled detection probe with respect to the non-target nucleic acid as described above, when the amount to be added is 10 or more at a molar ratio of the competitive probe/the fluorescent-labeled probe, there is a tendency that a peak due to mismatch hybridization of the fluorescent-labeled detection probe is sufficiently suppressed.

Although it depends on the sequence of the target nucleic acid to be detected itself, or which region of the sequence the detection or competitive probe covers, generally, as the difference between the Tm value of the competitive probe and the Tm value of the fluorescent-labeled detection probe with respect to the non-target nucleic acid becomes larger, the amount (molar ratio) to be added of the competitive probe/the fluorescent-labeled probe tends to become smaller. A person skilled in the art can easily determine the difference in Tm value and the amount to be added associated with the probes on the basis of the sequence of the target nucleic acid by a routine experiment based on the procedures according to the present invention.

Further, for example, as the conditions for the base length and the base sequence of each of the fluorescent-labeled detection probe and the competitive probe, the following conditions may be included:

(I) a region that hybridizes with the fluorescent-labeled detection probe in the target nucleic acid contains a region that hybridizes with the competitive probe;

(II) a region that hybridizes with the competitive probe in the target nucleic acid contains a region that hybridizes with the fluorescent-labeled detection probe; or (III) a region that hybridizes with the competitive probe in the target nucleic acid coincides with a region that hybridizes with the fluorescent-labeled detection probe.

Incidentally, the term "hybridizes" as used in the above (I) to (III) includes both perfect match hybridization and mismatch hybridization. In the case of (I) or (II), a narrower region of the region that hybridizes with the fluorescent-labeled detection probe and the region that hybridizes with the competitive probe corresponds to the target base sequence. In the case of (III), the fluorescent-labeled detection probe and the competitive probe both have the same base length as the target base sequence, and can mutually competitively hybridize with the perfectly matched region.

Hereinabove, examples of preferred conditions for the fluorescent-labeled detection probe and the competitive probe are exemplified. However, the fluorescent-labeled detection probe and the competitive probe may be any as long as when the above-mentioned procedures (a) to (c) are followed, a first order derivative curve for the control target reaction sample has a peak, but a first order derivative curve for the control non-target reaction sample does not substantially have a peak even other than those satisfying the conditions.

In the present invention, even if the non-target nucleic acid is contained in a reaction sample, mismatch hybridization of the fluorescent-labeled detection probe with the non-target nucleic acid is mostly inhibited by the competitive probe, and therefore, the non-target nucleic acid is not substantially detected by the fluorescent-labeled detection probe, or does not appear as a peak in a first order derivative curve of a temperature-fluorescence intensity curve. Then, only a case where a target nucleic acid is contained in a reaction sample, a peak due to hybridization of the fluorescent-labeled detection probe with the nucleic acid appears.

Accordingly, in the detection method according to the present invention, the presence or absence of the target base sequence can be clearly discriminated based on the presence or absence of a peak of a first order derivative curve of a temperature-fluorescence intensity curve. Further, the detection method according to the present invention has an advantage that even if a salt concentration in a reaction solution, which is a factor having an influence on the Tm value changes to some extent, the influence on the discrimination ability hardly occurs, and an accurate detection result can be stably obtained.

In addition to the steps (1) to (3) described above, the detection method according to the present invention may include:

(4) determining that the target base sequence (A) is present in the nucleic acid sample when the first order derivative curve obtained in (3) has a peak.

Here, the nucleic acid sample may also contain the non-target nucleic acid other than the target nucleic acid. In such a step (4), it is possible to easily determine the presence or absence of the target base sequence (A) according to whether the first order derivative curve of the temperature-fluorescence intensity curve obtained in the steps (1) to (3) has a shape having a peak or a shape having substantially no peak. Here, the description that the nucleic acid sample may also contain the non-target nucleic acid other than the target nucleic acid means that by this method, for example, in a genetic diagnosis or the like, it is also possible to easily determine the presence or absence of the target base sequence contained in a heterozygote of alleles.

<Method for Designing Probes>

The present invention can also provide a method for designing a fluorescent-labeled detection probe and a competitive probe that can be used in the above-mentioned detection method. The method includes:

(1') determining the base length and the base sequence of each of the fluorescent-labeled detection probe and the competitive probe according to (a) to (c) so that a first order derivative curve for a control target reaction sample has a peak (maximum value), but a first order derivative curve for a control non-target reaction sample does not substantially have a peak.

By such a method for designing probes, a probe set capable of detecting a single base difference of a SNP with high accuracy and easily determining the presence or absence of the target base sequence based on the presence or absence of a peak in the first order derivative curve of the temperature-fluorescence intensity curve can be realized.

<Method for Producing Probes>

Further, the present invention can also provide a method for producing a fluorescent-labeled detection probe and a competitive probe that can be used in the above-mentioned detection method. The method includes:

(1") synthesizing oligonucleotides having a base length and a base sequence of each designed according to the above-mentioned method for designing probes; and (2") labeling the oligonucleotide of the fluorescent-labeled detection probe with a fluorescent dye that can be used in the QP method.

The oligonucleotide may be artificially synthesized or biosynthesized, and the production method based on the sequence thereof has already been well known in this technical field, and a person skilled in the art can select an appropriate method.

<Kit>

Further, the present invention can also provide a kit to be used in the above-mentioned detection method. The kit according to the present invention includes the above-mentioned fluorescent-labeled detection probe and competitive probe, and an instruction manual. The instruction manual can include, e.g., information on a target base sequence that can be detected, information on the steps (1) to (3) or the steps (1) to (4) of the above-mentioned detection method, information on the amount to be added to a nucleic acid sample of each of the fluorescent-labeled detection probe and the competitive probe, etc.

The kit according to the present invention may be a kit to be used for a genetic diagnosis.

<Genetic Diagnosis Method>

Further, the present invention can also provide a genetic diagnosis method utilizing the above-mentioned detection method. The genetic diagnosis method according to the present invention includes:

(1-1) obtaining a nucleic acid sample containing a DNA region of a diagnostic target from a specimen containing a DNA;

(1-2) adding a detection probe labeled with a fluorescent dye that can be used in a QP (Quenching Probe/Primer) method and a competitive probe to the nucleic acid sample, thereby obtaining a reaction sample, so that the fluorescent-labeled detection probe or the competitive probe hybridizes with a target nucleic acid having a target base sequence (A) in the reaction sample;

(2) measuring a fluorescence intensity while changing the temperature of the reaction sample; and (3) performing first order differentiation of a temperature-fluorescence intensity curve obtained from the measurement results in (2), wherein the fluorescent-labeled detection probe and the competitive probe satisfy the same conditions (i) to (iii) as in the above-mentioned method for detecting a target base sequence. In order to make the determination of the presence or absence of a gene having a target base sequence easier, the genetic diagnosis method according to the present invention may include the step (4) (determining that the target base sequence (A) is present in the nucleic acid sample when the first order derivative curve obtained in (3) has a peak) of the above-mentioned detection method.

Further, in the genetic diagnosis method according to the present invention, in order to make the method further simpler, as a means for obtaining a nucleic acid sample sufficiently containing a nucleic acid of a DNA region of a diagnostic target in the step (1-1), the nucleic acid of the DNA region may be amplified by a LAMP method. Accordingly, the genetic diagnosis method that is simple and takes a short time as compared with a currently available genetic diagnosis method using, for example, a PCR method can be provided. Incidentally, the nucleic acid after amplification by the LAMP method in this method is an example of the "the nucleic acid sample derived from a living body" as described above.

The following Examples further specifically describe the present invention and by no means limit the scope of the invention. A person possessing ordinary knowledge and skills as a person skilled in the art can make various modifications to embodiments shown in the following Examples without departing from the spirit of the invention, and the modified embodiments are also included in the invention.

A person skilled in the art can appropriately design a fluorescent-labeled detection probe and a competitive probe capable of achieving the effects of the present invention with respect to base sequences of various targets with reference to the following Examples, and excessive trial and error are not required.

WORKING EXAMPLES

Example 1: Detection of rpoB Gene Mutation by Adding Competitive Probe

By using the method for detecting a target base sequence according to the present invention, single base mutation detection was performed by targeting a resistance determining region of a rpoB gene associated with acquisition of rifampicin resistance in *Mycobacterium tuberculosis* (rifampicin resistance determining region, RRDR). In this single base mutation detection, a mutation in which by substituting one base in the $516^{th}$ codon of a base sequence of a rpoB gene from A to T, an amino acid encoded thereby is substituted from Asp to Val was targeted. A base sequence of a region containing this mutation site is represented by a "target nucleic acid having a target base sequence" (A allele) or a "non-target nucleic acid having a non-target base sequence" (T allele). Incidentally, Example 1 corresponds to an example in which a "target base sequence containing a nucleotide with a mutated base" is determined to be a wild-type base sequence and a "non-target base sequence" containing a "nucleotide with an unmutated base" is determined to be a mutant-type base sequence, and whether or not the wild-type base sequence is contained in a nucleic acid sample is determined.

Here, as a premise, in Example 1, the sense strand of the target base sequence in the A allele has "A" at the above-mentioned mutation site and the sense strand of the non-target base sequence in the T allele has "T" at the above-mentioned mutation site, however, in fact, a target with which the detection probe or the competitive prove is allowed to hybridize is the antisense strand of the base sequence of each probe. Therefore, when the contents of Example 1 are compared with the description of the claims appended to this application, an antisense strand complementary to the sense strand of the A allele corresponds to an example of the "target nucleic acid" in the claims, and the "antisense strand of a target base sequence" complementary to the "sense strand of the target base sequence" corresponds to an example of the "target base sequence" in the claims.

Similarly, the antisense strand of the T allele corresponds to an example of the "non-target nucleic acid" in the claims, and the antisense strand of the non-target base sequence corresponds to an example of the "non-target base sequence" in the claims.

A detection probe (RB516A-2) containing an oligonucleotide of the same base sequence as the sense strand of the target base sequence was designed by using a base sequence within a given range containing the nucleotide "A" at the mutation site in the A allele ("T" of the antisense strand complementary thereto corresponds to an example of the "nucleotide with a mutated base" in the claims) as the sense strand of the target base sequence. With respect to a non-target base sequence that is a base sequence within the same range as the range of the target base sequence in the A allele (that is, the same base sequence as the above-mentioned target base sequence except that the nucleotide "A" ("T" in the antisense strand of the A allele) at the above-mentioned mutation site is replaced with a nucleotide "T" ("A" in the antisense strand of the T allele) after a single base mutation) in the T allele, a competitive probe (RB516T-2-P) containing an oligonucleotide of the same base sequence as the sense strand of this non-target base sequence was designed. Incidentally, in the above description, "A" in the antisense strand of the T allele that is complementary to the nucleotide "T" at the mutation site in the T allele corresponds to an example of the "nucleotide with an unmutated base" in the claims. Further, as described above, by using the same base sequence as the sense strand of each base sequence, the detection probe (RB516A-2) has a base sequence complementary to the antisense strand of the target base sequence ("target base sequence" in the claims), and the competitive probe (RB516T-2-P) has a base sequence complementary to the antisense strand of the non-target base sequence ("non-target base sequence" in the claims). These oligonucleotides having the thus designed base length and base sequence were synthesized, respectively, and the detection probe was labeled with a fluorescent dye TAMRA™, whereby the fluorescent-labeled detection probe and the competitive probe were produced. Incidentally, the competitive probe was not labeled with a fluorescent dye, but modified with a phosphate group.

TABLE 1

PROBES USED IN EXAMPLE 1

| PROBE TYPE | PROBE NAME | SEQUENCE | SEQ. ID NO |
|---|---|---|---|
| Fluorescent-labeled detection probe | RB516A-2 | AATTCATGGACCAGAACAAC-TAMRA | 1 |
| Competitive probe | RB516T-2-P | AATTCATGGTCCAGAACAAC-P | 2 |

A nucleic acid sample was prepared as follows:

With respect to each of a gene sequence in which the sequence of the above-mentioned rpoB RRDR is a mutant type and a gene sequence in which the sequence at a single base mutation site thereof is a wild type, a sample obtained by treating a plasmid prepared by subcloning the following region in the genomic DNA A:

Mycobacterium tuberculosis H37Rv ID: ref|NC_000962.3|760767-761516 (searchable in GenBank of National Center for Biotechnology Information, NCBI (NCBI) in the USA) with restriction enzymes (XbaI/XhoI) was used as a template. More specifically, the sequence of H37Rv thereof was acquired from the database, and a plasmid artificially mutated so as to have a drug resistant sequence (mutant type) was prepared (employing artificial gene synthesis service of Eurofins Genomics K.K.) and used. Similarly, a plasmid of a sensitive sequence (wild type) was also synthesized, and as for a heterozygote, the synthesized wild-type and mutant-type plasmids were mixed and used.

With respect to the above-mentioned templates, a LAMP reaction was performed at 65° C. for 90 minutes using the following primers. The LAMP reaction was performed using a Loopamp® real-time turbidity measuring device LA200 (Teramecs).

TABLE 2

PRIMERS USED IN LAMP REACTION

| PRIMER NAME | SEQUENCE | SEQ ID NO |
|---|---|---|
| rpoB-F-ID-H-FIP | CTCACGTGACAGACCGCCGGCCGCGATCAAGGAGTTC | 3 |
| rpoB-F-ID1-BIP-22 | CACCCGTCGCACTACGTTGGGCCCCTCAGG | 4 |

TABLE 2-continued

PRIMERS USED IN LAMP REACTION

| PRIMER NAME | SEQUENCE | SEQ ID NO |
|---|---|---|
| rpoB-F-ID-H-FL | TGGCTGGTGCCGAAG | 5 |
| rpoB-F-ID1-BL-1 | CGGATGTGCCCGATCGAA | 6 |
| rpoB-F-ID-H-F3 | CAGACGTTGATCAACATCCG | 7 |
| rpoB-F-ID1-B3-2 | CGCGTACACCGACAGC | 8 |

The composition (in 25 μm) of the reaction solution was set as follows:

20 mM Tricine pH 8.8, 50 mM KCl, 8 mM MgSO4, 1.4 mM ATP, 1.4 mM GTP, 1.4 mM CTP, 1.4 mM TTP, 0.5% Tween 20, 16 U Bst-Large Fragment Further, before the LAMP amplification reaction, the fluorescent-labeled detection probe (final concentration: 0.04 μM) and the competitive probe (final concentration: 1.2 μM) were added. The reason why the probes were added before the LAMP amplification reaction at that point is to prevent the increase in the risk of amplification product carry-over contamination when a container containing the amplification product is opened after the reaction.

By the above-mentioned reaction, the T allele in the mutant-type template and the A allele in the wild-type template were specifically amplified, respectively. By doing this, reaction samples corresponding to samples in which the fluorescent-labeled detection probe (final concentration: 0.04 μM) and the competitive probe (final concentration: 1.2 μM) were added to the amplification products were obtained. These reaction samples were heated at 99° C. for 5 minutes using a device MX3005p (Agilent Technologies), and thereafter cooled at a rate of −2° C./30 sec, and a fluorescence value was measured at every 30 seconds. With respect to data corresponding to a temperature-fluorescence intensity curve obtained by the measurement, a derivative value was calculated using a dedicated software for MX3005p (Agilent Technologies). First order derivative curves (thermal dissociation curves) shown in FIG. 1 were obtained.

As shown by the experimental data of FIG. 1, by adding the competitive probe having the same base sequence as the sense strand of the non-target base sequence of the same region as the target base sequence, a detection system in which when the target base sequence is present in the reaction sample, a peak (quenching peak) appears in the thermal dissociation curve, and when the target base sequence is not substantially contained in the reaction sample, a peak does not substantially appear could be realized.

According to this detection system, when the above-mentioned detection method is applied with respect to the target nucleic acid (A allele) derived from an individual having no wild-type single base mutation, the obtained thermal dissociation curve has a peak, and therefore, it can be determined that the individual is a wild type having no mutant-type single base mutation, and on the other hand, when the above-mentioned detection method is applied with respect to the non-target nucleic acid (T allele) derived from an individual having a mutant-type single base mutation, the obtained thermal dissociation curve does not have a peak, and therefore, it can be determined that the individual does not have a wild-type target nucleic acid.

Further, a similar experiment was performed also for a mixture of the target nucleic acid (A allele) and the non-target nucleic acid (T allele) by assuming a case where the nucleic acid sample is derived from the allele and the genotype of a single base mutation is a mutant-type/wild-type heterozygote. An obtained thermal dissociation curve (indicated by a long dashed short dashed line in FIG. 1) has a weaker peak as compared with the peak obtained in the case of only the target nucleic acid (A allele). Therefore, since the thermal dissociation curve has a peak, it can be determined that the individual has a wild-type unmutated single base. Further, it is suggested that a semi-quantitative determination for predicting whether the genotype of the single base mutation is a wild-type homozygote or a mutant-type/wild-type heterozygote based on the peak intensity is also possible depending on the conditions for the detection probe and the competitive probe.

Example 2: Conditions for Designing Competitive Probe (1) (Comparison with Partial Competitive-Type Probe)

With respect to the same rpoB RRDR gene as in Example 1, conditions for designing probes for detecting a single base mutation were examined. A target nucleic acid (A allele, SEQ ID NO: 9 (a sequence viewed in the 3'→5' direction)) having a target base sequence and a non-target nucleic acid (T allele, SEQ ID NO: 10 (a sequence viewed in the 3'→5' direction)) having a non-target base sequence as shown in FIG. 2 were used for a control target nucleic acid sample and a control non-target nucleic acid sample, respectively. With respect to these target nucleic acid and non-target nucleic acid, a detection probe and a competitive probe having the same base sequence (that is, complementary to each of the target base sequence in the base sequence represented by SEQ ID NO: 9 and the non-target base sequence in the base sequence represented by SEQ ID NO: 10) as the sense strand of the target base sequence and the sense strand of the non-target base sequence were designed, respectively. These detection probe and competitive probe mutually have the same base length and mutually have the same base sequence except that one base complementary to the nucleotide ("T" or "A") at a mutation site is different.

In order to compare with a case where the competitive probe in the present invention was used, two partial competitive-type probes were designed. A partial competitive-type probe 1 and a partial competitive-type probe 2 were designed so that a portion of the base sequence thereof can hybridize with a region common to the detection probe in the target nucleic acid.

In this Example, in order to examine the conditions for designing the competitive probe, with respect to each of the reaction samples obtained by adding the detection probe (final concentration: 0.04 μM) and the competitive probe (final concentration: 1.2 μM) to each of a nucleic acid sample (control target nucleic acid sample) that contains the target nucleic acid, but does not substantially contain the non-target nucleic acid and a nucleic acid sample (control non-target nucleic acid sample) that does not substantially contain the target nucleic acid, but contains the non-target nucleic acid, a fluorescence intensity was measured while changing the temperature in the same manner as in Example 1.

Similarly, also with respect to each of the reaction samples obtained by adding the detection probe (final concentration: 0.04 μM) and the partial competitive-type probe 1 or 2 (final concentration: 1.2 μM) to each of the control target nucleic acid sample and the control non-target nucleic acid sample, a fluorescence intensity was measured while changing the temperature.

Further, as a control experiment, only the detection probe (final concentration: 0.04 μM) was added to each of the control target nucleic acid sample and the control non-target nucleic acid sample, and a fluorescence intensity was measured while changing the temperature. The results are shown in FIG. 3-1.

As shown in FIG. 3-2, when only the detection probe was used or when the partial competitive-type probe was used together with the detection probe, a first order derivative curve of a temperature-fluorescence intensity curve obtained for the control non-target nucleic acid sample had a quenching peak at the lower temperature side than a quenching peak of a first order derivative curve for the control target nucleic acid sample. This is a quenching peak due to mismatch hybridization of the detection probe with the non-target nucleic acid. For example, depending on the conditions such as a salt concentration, a temperature at which a quenching peak due to this mismatch hybridization appears shifts to a higher temperature in some cases, and there is a possibility that this peak may be misidentified as a quenching peak due to perfect match hybridization of the detection probe with the target nucleic acid.

On the other hand, when the above-mentioned competitive probe was used together with the detection probe, a first order derivative curve for the control non-target nucleic acid sample did not substantially have a quenching peak. Therefore, this competitive probe can be used together with the above-mentioned detection probe in the detection method of the present invention, and by using this competitive probe, a detection system in which a quenching peak does not substantially appear if the target nucleic acid is not substantially contained can be realized.

It can be said that this result is an example that clearly demonstrated the remarkability of the effects of the present invention with respect to the invention described in PTL 1.

Example 3: Conditions for Designing Competitive Probe (2) (Regarding Tm Value)

With respect to the same rpoB RRDR gene as in Example 1 and Example 2, in order to examine Tm value conditions for designing a competitive probe, a binding strength of each of the fluorescent-labeled detection probe and the competitive probe to each of the target nucleic acid and the non-target nucleic acid was calculated as a Tm value, and a relationship between the Tm value and the presence or absence of the above-mentioned quenching peak in a first order derivative curve of a temperature-fluorescence intensity curve was examined.

In this Example, unlike Example 1 and Example 2, the target nucleic acid was determined to be the T allele (mutant-type base sequence) and the non-target nucleic acid was determined to be the A allele (wild-type base sequence). That is, the target nucleic acid (T allele, SEQ ID NO: 10 (a sequence viewed in the 3'→5' direction)) having a target base sequence and the non-target nucleic acid (A allele, SEQ ID NO: 9 (a sequence viewed in the 3'→5' direction)) having a non-target base sequence were used for a control target nucleic acid sample and a control non-target nucleic acid sample, respectively. In this Example, a fluorescent-labeled probe (as a fluorescent-labeled detection probe) was prepared by labeling a detection probe perfectly matched with the T allele (that is, perfectly complementary to the target base sequence in the base sequence represented by SEQ ID NO: 10) with a fluorescent dye BODIPY® FL. Further, 10 types of competitive probes perfectly matched with the A allele (that is, perfectly complementary to the non-target base sequence in the base sequence represented by SEQ ID NO: 9) and having a different Tm value were prepared. The plurality of competitive probes having a different Tm value were prepared by variously changing the base length of the competitive probe with respect to the fluorescent-labeled probe from a base length which is shorter than that of the fluorescent-labeled probe by several bases to a base length which is longer than that of the fluorescent-labeled probe by several bases.

By using the one type of fluorescent-labeled probe (final concentration: 0.04 μM) perfectly matched with the T allele and the 10 types of competitive probes perfectly matched with the A allele and having a different Tm value (final concentration: 1.2 μM), the presence or absence of a quenching peak was measured in the same manner as in Example 1. The Tm value of each of the fluorescent-labeled probe and the competitive probes with respect to each of the target nucleic acid and the non-target nucleic acid was as shown in the table in FIG. 4-2 and the graph in FIG. 4-3. The Tm values for perfect match (the fluorescent-labeled probe with respect to the T allele and the competitive probe with respect to the A allele) and mismatch (the fluorescent-labeled probe with respect to the A allele and the competitive probe with respect to the T allele) were calculated using Meltcalc 99 free (http://www.meltcalc.com/) under the set condition: Na eq. [mM] 50.

As a result, as shown in FIG. 4-2 and FIG. 5, when the Tm value of the competitive probe with respect to the A allele (perfect match with A allele) was higher than the Tm value of the fluorescent-labeled probe (perfect match with T allele) by 10.1° C. or more (when "RB516A-3-P-7", "RB516A-3-P-8", "RB516A-3-P-9", or "RB516A-3-P-10" was used as the competitive probe), a quenching peak when using the A allele as a template disappeared.

On the other hand, when the Tm value of the competitive probe with respect to the T allele (perfect match with A allele) became higher than the Tm value of the fluorescent-labeled probe (perfect match with T allele) by −1.8° C. or more, a quenching peak when the T allele was used as a template is attenuated in a stepwise manner, and when it became higher by 9.9° C. (when "RB516A-3-P-9" or "RB516A-3-P-10" was used as the competitive probe), a quenching peak when using the T allele as a template disappeared. This is considered to be because theoretically, when the Tm value of the competitive probe with respect to the target nucleic acid is higher than the Tm value of the fluorescent-labeled detection probe, the competitive probe more stably hybridizes with the target nucleic acid than the fluorescent-labeled detection probe, and therefore, hybridization of the fluorescent-labeled detection probe with the target nucleic acid is inhibited, and detectable quenching is reduced.

From this experiment, it is found that when a combination of the fluorescent-labeled probe "RB516T-3b" with the competitive probe "RB516A-3-P-7" or a combination of the fluorescent-labeled probe "RB516T-3b" with the competitive probe "RB516A-3-P-8" was used, a first order derivative curve for the control target reaction sample (the sample containing the T allele) has a quenching peak, however, a first order derivative curve for the control non-target reaction sample (the sample containing the A allele) does not substantially have a quenching peak, and a probe set of such a combination can be determined to be favorable.

It was found that as the Tm value conditions in this example, it is preferred that with respect to the non-target nucleic acid, the Tm value of the competitive probe is higher than the Tm value of the fluorescent-labeled probe by 10.1° C. or more and also with respect to the target nucleic acid, the Tm value of the competitive probe is lower than the Tm value of the fluorescent-labeled probe.

Further, in this example, even if with respect to the target nucleic acid, the Tm value of the competitive probe exceeds the Tm value of the fluorescent-labeled probe, when the difference is 6.1° C. or less, a first order derivative curve for the control target reaction sample has a quenching peak, and a first order derivative curve for the control non-target reaction sample does not substantially have a quenching peak, and therefore, it is considered that this can sufficiently applied to the present invention. Therefore, for example, conditions in which with respect to the non-target nucleic acid, the Tm value of the competitive probe is higher than the Tm value of the fluorescent-labeled probe by at least 10° C. and also with respect to the target nucleic acid, the Tm value of the competitive probe does not exceed the Tm value of the fluorescent-labeled probe+6.1° C., more preferably does not exceed the Tm value of the fluorescent-labeled probe+5° C. can also be said to be an example of other preferred Tm value conditions.

Here, when with respect to the target nucleic acid, the Tm value of the competitive probe exceeds the Tm value of the fluorescent-labeled probe, there is a tendency that the Tm value of the competitive probe with respect to the non-target nucleic acid also becomes further higher, and for example, the Tm value of the competitive probe with respect to the non-target nucleic acid can become higher than the Tm value of the fluorescent-labeled probe by 15° C. or more (specifically, when referring to FIG. 4-2, in the case where the competitive probe "RB516A-3-P-8" is used, the Tm value of the competitive probe is higher than that of the fluorescent-labeled probe by 16.8° C.). Therefore, for example, conditions in which with respect to the non-target nucleic acid, the Tm value of the competitive probe is higher than the Tm value of the fluorescent-labeled probe by at least 15° C. and with respect to the target nucleic acid, the Tm value of the competitive probe does not exceed the Tm value of the fluorescent-labeled probe+5° C. can also be said to be an example of other preferred Tm value conditions.

Incidentally, in the above-mentioned Example 1 and Example 2, an example in which the target base sequence having a wild-type base sequence is detected is described, and in the above-mentioned Example 3, on the contrary to the above-mentioned Example 1 and Example 2, an example in which conditions for designing probes for detecting a mutant-type base sequence are examined is described, however, whether the target base sequence is determined to be a wild-type base sequence or a mutant-type base sequence is not particularly limited. For example, the method described in the above-mentioned Example 3 may be applied to an examination of conditions for designing probes for detecting a wild-type base sequence on the contrary to the above-mentioned Example 3. When such a change is made, it is only necessary to design one fluorescent-labeled probe perfectly matched with the A allele and a plurality of competitive probes perfectly matched with the T allele and having a different Tm value, respectively, and measure the presence or absence of a quenching peak in the same manner as described above.

Example 4: Example of Examining Conditions (Tm Value) for Designing Probes for Detecting Single Base Mutation with Respect to Other Genes The present inventors demonstrated that the detection method of the present invention can also be applied to detection of a single base mutation other than in rpoB RRDR. In this Example, unlike Examples 1 to 3, in order to discriminate a specific single base mutation in a human gene, conditions (Tm value) for designing a detection probe and a competitive probe were examined. In this Example, first, a target base sequence having an appropriate length containing a single base mutation site to be targeted was determined, and a detection probe complementary to the target base sequence was prepared and labeled with a fluorescent dye, thereby forming a fluorescent-labeled detection probe. Further, conditions for designing probes for detecting a single base mutation were examined by performing an experiment in which the base length of the competitive probe with respect to the same detection probe was variously changed from a base length which is shorter than that of the detection probe by several bases to a base length which is longer than that of the detection probe by several bases, and a first order derivative curve is determined with respect to a control target reaction sample and a control non-target reaction sample as described above. From this experiment, results that as the conditions for the base length and the base sequence of each of the competitive probes, when with respect to the non-target nucleic acid, the Tm value of the competitive probe is higher than the Tm value of the detection probe by at least 5° C., and with respect to the target nucleic acid, the Tm value of the competitive probe is lower than the Tm value of the detection probe, and the amount (molar ratio) to be added of the competitive probe/the fluorescent-labeled detection probe is 30/1, a first order derivative curve for the control target reaction sample has a quenching peak, but a first order derivative curve for the control non-target reaction sample does not substantially have a quenching peak (alternatively, even if it has a quenching peak, it is apparently a weak quenching peak as compared with the quenching peak of the first order derivative curve for the control target reaction sample, and it can be apparently discriminated from the case of the control target reaction sample) were obtained.

However, when a difference between the Tm value of the competitive probe with respect to the non-target nucleic acid and the Tm value of the detection probe was less than 5° C., a quenching peak due to mismatch hybridization of the detection probe with the non-target nucleic acid was not suppressed, and as a result, also in the first order derivative curve for the control non-target reaction sample, a quenching peak similar to that in the first order derivative curve for the control target reaction sample was observed. On the other hand, when with respect to the target nucleic acid, the Tm value of the competitive probe was set higher than the Tm value of the detection probe, a result that the quenching peak itself by the detection of the target nucleic acid becomes smaller was obtained. This is because the competitive probe more stably hybridizes with the target nucleic acid than the detection probe, and therefore, detection by hybridization of the detection probe with the target nucleic acid is inhibited.

Further, it was found that when the same conditions as the above-mentioned conditions were set except that with respect to the non-target nucleic acid, the Tm value of the competitive probe was set higher than the Tm value of the detection probe by at least 15° C. in the above-mentioned conditions, as compared with a case where with respect to the same non-target nucleic acid, the Tm value of the competitive probe was set higher than the Tm value of the detection probe by about 5 to 10° C., the shape of the first order derivative curve for the control non-target reaction sample approaches a flatter shape. From this result, it is considered that in the present invention, by enhancing the specificity (thermal stability of hybridization) of the competitive probe for the non-target nucleic acid with respect to the thermal stability of hybridization of the detection probe with the non-target nucleic acid, a quenching peak due to mismatch hybridization with low specificity can be more reliably suppressed.

As can be found from the results of the above-mentioned Example 3 and Example 4, preferred Tm value conditions vary depending on the sequence of the target nucleic acid to be detected itself, or which region of the sequence the fluorescent-labeled detection probe or the competitive probe covers, and further can change in a complicated manner depending on the concentration of each probe to be added, a salt concentration in a sample, etc. However, a person skilled in the art can determine the base length and the base sequence of each of the fluorescent-labeled detection probe and the competitive probe for achieving the effects of the present invention by performing an experiment based on the procedures according to the present invention with reference to the preferred Tm values found from the above-mentioned Example 3 and Example 4, and excessive trial and error are not required.

INDUSTRIAL APPLICABILITY

The present invention provides a means for simply and reliably discriminating a difference of one base such as a SNP, and also can realize simplification of a SNP typing technique by making strict management of the conditions such as a salt concentration in a reaction sample that would affect a Tm value unnecessary unlike a conventional method, and has a possibility of wide application to genetic testing, drug discovery, medical diagnosis, and so on.

The invention claimed is:

1. A method for detecting a target base sequence (A) containing a nucleotide with a mutated base from a nucleic acid sample, the method comprising the following steps:
   (1) adding a detection probe labeled with a fluorescent dye that can be used in a QP (Quenching Probe/Primer) method and a competitive probe to the nucleic acid sample, thereby obtaining a reaction sample, so that the fluorescent-labeled detection probe or the competitive probe hybridizes with a target nucleic acid having the target base sequence (A) in the reaction sample;
   (2) measuring a fluorescence intensity while changing the temperature of the reaction sample;
   (3) performing first order differentiation of a temperature-fluorescence intensity curve obtained from the measurement results in (2); and,
   (4) detecting the target base sequence (A) containing the nucleotide with the mutated base in the nucleic acid sample, the detecting including
      measuring for a presence of a substantial quenching peak in the thermal dissociation curve of the nucleic acid sample when the target base sequence is present in the reaction sample; and,
      measuring for an absence of a substantial quenching peak in the thermal dissociation curve of the nucleic acid sample when the target base sequence is not substantially contained in the reaction sample;
   wherein, the adding includes
      (i) designing the base sequence of the fluorescent-labeled detection probe to contain a base sequence (A') complementary to the target base sequence (A),
      (ii) designing the base sequence of the competitive probe to contain a base sequence (B') complementary to a non-target base sequence (B) that is the same base sequence as the target base sequence (A) except that the nucleotide with a mutated base is replaced with a nucleotide with an unmutated base, and
      (iii) experimentally determining the amount to be added to the nucleic acid sample of each of the fluorescent-labeled detection probe and the competitive probe, the experimentally determining including:
         (a) adding the fluorescent-labeled detection probe and the competitive probe to each of
         a control target nucleic acid sample that contains the target nucleic acid, but does not substantially contain a non-target nucleic acid having the non-target base sequence (B); and,
         a control non-target nucleic acid sample that does not substantially contain the target nucleic acid, but contains the non-target nucleic acid;
         (b) measuring a fluorescence intensity while changing the temperature of each of the control reaction samples; and,
         (c) performing first order differentiation of each of the temperature-fluorescence intensity curves obtained from the measurement results,
         wherein the adding, measuring, and performing are done so that a functional result of a first order derivative curve for the control target reaction sample has a substantial peak (maximum value), but a first order derivative curve for the control non-target reaction sample does not have a substantial peak.

2. The method according to claim 1, further comprising the following step:
   (4) determining that the target base sequence (A) is present in the nucleic acid sample when the first order derivative curve obtained in (3) has a peak, wherein the nucleic acid sample may also contain a non-target nucleic acid other than the target nucleic acid.

3. The method according to claim 1, wherein
   with respect to the non-target nucleic acid, the Tm value of the competitive probe is higher than the Tm value of the fluorescent-labeled detection probe by at least 5° C., and with respect to the target nucleic acid, the Tm value of the competitive probe is lower than the Tm value of the fluorescent-labeled detection probe.

4. The method according to claim 1, wherein
with respect to the non-target nucleic acid, the Tm value of the competitive probe is higher than the Tm value of the fluorescent-labeled detection probe by at least 10° C., and
with respect to the target nucleic acid, the Tm value of the competitive probe is lower than the Tm value of the fluorescent-labeled detection probe.

5. The method according to claim 1, wherein
with respect to the non-target nucleic acid, the Tm value of the competitive probe is higher than the Tm value of the fluorescent-labeled detection probe by at least 10° C., and
with respect to the target nucleic acid, the Tm value of the competitive probe does not exceed the Tm value of the fluorescent-labeled detection probe+5° C.

6. The method according to claim 1, wherein
with respect to the non-target nucleic acid, the Tm value of the competitive probe is higher than the Tm value of the fluorescent-labeled detection probe by at least 15° C., and
with respect to the target nucleic acid, the Tm value of the competitive probe does not exceed the Tm value of the fluorescent-labeled detection probe+5° C.

7. The method according to claim 1, wherein
with respect to the non-target nucleic acid, the Tm value of the competitive probe is higher than the Tm value of the fluorescent-labeled detection probe by at least 15° C., and
with respect to the target nucleic acid, the Tm value of the competitive probe is lower than the Tm value of the fluorescent-labeled detection probe.

8. The method according to claim 1, wherein
(I) a region that hybridizes with the fluorescent-labeled detection probe in the target nucleic acid contains a region that hybridizes with the competitive probe;
(II) a region that hybridizes with the competitive probe in the target nucleic acid contains a region that hybridizes with the fluorescent-labeled detection probe; or
(III) a region that hybridizes with the competitive probe in the target nucleic acid coincides with a region that hybridizes with the fluorescent-labeled detection probe.

9. The method according to claim 1, wherein the amount to be added of the competitive probe to the nucleic acid sample is at least 10 times (molar ratio) the amount to be added of the fluorescent-labeled detection probe.

10. The method according to claim 1, wherein the amount to be added of the competitive probe to the nucleic acid sample is at least 20 times (molar ratio) the amount to be added of the fluorescent-labeled detection probe.

11. The method according to claim 1, wherein the fluorescent dye that can be used in the QP (Quenching Probe/Primer) method is at least one type of fluorescent dye selected from the group consisting of tetramethyl rhodamine; 4,4-difluoro-5,7-dimethyl-4-bora-3a,4a-diaza-s-indacen-3-propionic acid;
3-carboxy-6,8-difluoro-7-hydroxycoumarin; and carboxy rhodamine 6G.

12. The method according to claim 1, wherein the nucleic acid sample is derived from a living body.

13. The method according to claim 1, wherein the nucleotide with a mutated base is a DNA containing a single base substitution mutation.

* * * * *

SEQUENCE LISTING

```
<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Designed oligonucleotides as a detection probe

<400> SEQUENCE: 1
aattcatgga ccagaacaac                                                   20

<210> SEQ ID NO 2
<211> LENGTH: 20
<212> TYPE: DNA
<213> ORGANISM: Artificial Sequence
<220> FEATURE:
<223> OTHER INFORMATION: Designed oligonucleotides as a competitive
      probe

<400> SEQUENCE: 2
aattcatggt ccagaacaac                                                   20

<210> SEQ ID NO 3
<211> LENGTH: 37
<212> TYPE: DNA
<213> ORGANISM: Artificial Sequence
<220> FEATURE:
<223> OTHER INFORMATION: primer

<400> SEQUENCE: 3
ctcacgtgac agaccgccgg ccgcgatcaa ggagttc                                 37

<210> SEQ ID NO 4
<211> LENGTH: 30
<212> TYPE: DNA
<213> ORGANISM: Artificial Sequence
<220> FEATURE:
```

```
<223> OTHER INFORMATION: primer

<400> SEQUENCE: 4
cacccgtcgc actacgttgg gccccctcagg                                        30

<210> SEQ ID NO 5
<211> LENGTH: 15
<212> TYPE: DNA
<213> ORGANISM: Artificial Sequence
<220> FEATURE:
<223> OTHER INFORMATION: primer

<400> SEQUENCE: 5
tggctggtgc cgaag                                                         15

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
cggatgtgcc cgatcgaa                                                      18

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
cagacgttga tcaacatccg                                                    20

<210> SEQ ID NO 8
<211> LENGTH: 16
<212> TYPE: DNA
<213> ORGANISM: Artificial Sequence
<220> FEATURE:
<223> OTHER INFORMATION: primer

<400> SEQUENCE: 8
cgcgtacacc gacagc                                                        16

<210> SEQ ID NO 9
<211> LENGTH: 49
<212> TYPE: DNA
<213> ORGANISM: Mycobacterium tuberculosis

<400> SEQUENCE: 9
gtcaaccccg acagcgggtt gttctggtcc atgaattggc tcagctggc                    49

<210> SEQ ID NO 10
<211> LENGTH: 49
<212> TYPE: DNA
<213> ORGANISM: Mycobacterium tuberculosis

<400> SEQUENCE: 10
gtcaaccccg acagcgggtt gttctggacc atgaattggc tcagctggc                    49

<210> SEQ ID NO 11
<211> LENGTH: 23
<212> TYPE: DNA
<213> ORGANISM: Artificial Sequence
```

```
<220> FEATURE:
<223> OTHER INFORMATION: Designed oligonucleotides as a detection probe

<400> SEQUENCE: 11
ccaattcatg gaccagaaca acc                                              23

<210> SEQ ID NO 12
<211> LENGTH: 23
<212> TYPE: DNA
<213> ORGANISM: Artificial Sequence
<220> FEATURE:
<223> OTHER INFORMATION: Designed oligonucleotides as a competitive
      probe complementary to T allele

<400> SEQUENCE: 12
ccaattcatg gtccagaaca acc                                              23

<210> SEQ ID NO 13
<211> LENGTH: 23
<212> TYPE: DNA
<213> ORGANISM: Artificial Sequence
<220> FEATURE:
<223> OTHER INFORMATION: Designed oligonucleotides as a partially-
      competetive probe complement to T allele

<400> SEQUENCE: 13
tggtccagaa caacccgctg tcg                                              23

<210> SEQ ID NO 14
<211> LENGTH: 23
<212> TYPE: DNA
<213> ORGANISM: Artificial Sequence
<220> FEATURE:
<223> OTHER INFORMATION: Designed oligonucleotides as a partially-
      competetive probe complement to T allele

<400> SEQUENCE: 14
gtccagaaca acccgctgtc ggg                                              23

<210> SEQ ID NO 15
<211> LENGTH: 23
<212> TYPE: DNA
<213> ORGANISM: Artificial Sequence
<220> FEATURE:
<223> OTHER INFORMATION: Designed oligonucleotides as a detection probe
      RB516T-3b

<400> SEQUENCE: 15
ccaattcatg gtccagaaca acc                                              23

<210> SEQ ID NO 16
<211> LENGTH: 15
<212> TYPE: DNA
<213> ORGANISM: Artificial Sequence
<220> FEATURE:
<223> OTHER INFORMATION: Designed oligonucleotides as a partially-
      competetive probe RB516A-3-P-1 complement to A allele

<400> SEQUENCE: 16
ttcatggacc agaac                                                       15

<210> SEQ ID NO 17
<211> LENGTH: 17
<212> TYPE: DNA
<213> ORGANISM: Artificial Sequence
<220> FEATURE:
<223> OTHER INFORMATION: Designed oligonucleotides as a partially-
``` competetive probe RB516A-3-P-2 complement to A allele

<400> SEQUENCE: 17
attcatggac cagaaca                                                      17

<210> SEQ ID NO 18
<211> LENGTH: 19
<212> TYPE: DNA
<213> ORGANISM: Artificial Sequence
<220> FEATURE:
<223> OTHER INFORMATION: Designed oligonucleotides as a partially-
      competetive probe RB516A-3-P-3 complement to A allele

<400> SEQUENCE: 18
aattcatgga ccagaacaa                                                    19

<210> SEQ ID NO 19
<211> LENGTH: 20
<212> TYPE: DNA
<213> ORGANISM: Artificial Sequence
<220> FEATURE:
<223> OTHER INFORMATION: Designed oligonucleotides as a partially-
      competetive probe RB516A-3-P-4 complement to A allele

<400> SEQUENCE: 19
caattcatgg accagaacaa                                                   20

<210> SEQ ID NO 20
<211> LENGTH: 21
<212> TYPE: DNA
<213> ORGANISM: Artificial Sequence
<220> FEATURE:
<223> OTHER INFORMATION: Designed oligonucleotides as a partially-
      competetive probe RB516A-3-P-5 complement to A allele

<400> SEQUENCE: 20
caattcatgg accagaacaa c                                                 21

<210> SEQ ID NO 21
<211> LENGTH: 22
<212> TYPE: DNA
<213> ORGANISM: Artificial Sequence
<220> FEATURE:
<223> OTHER INFORMATION: Designed oligonucleotides as a partially-
      competetive probe RB516A-3-P-6 complement to A allele

<400> SEQUENCE: 21
ccaattcatg gaccagaaca ac                                                22

<210> SEQ ID NO 22
<211> LENGTH: 23
<212> TYPE: DNA
<213> ORGANISM: Artificial Sequence
<220> FEATURE:
<223> OTHER INFORMATION: Designed oligonucleotides as a partially-
      competetive probe RB516A-3-P-7 complement to A allele

<400> SEQUENCE: 22
ccaattcatg gaccagaaca acc                                               23

<210> SEQ ID NO 23
<211> LENGTH: 27
<212> TYPE: DNA
<213> ORGANISM: Artificial Sequence
<220> FEATURE:
<223> OTHER INFORMATION: Designed oligonucleotides as a partially-
      competetive probe RB516A-3-P-8 complement to A allele

```
<400> SEQUENCE: 23
agccaattca tggaccagaa caacccg                                       27

<210> SEQ ID NO 24
<211> LENGTH: 31
<212> TYPE: DNA
<213> ORGANISM: Artificial Sequence
<220> FEATURE:
<223> OTHER INFORMATION: Designed oligonucleotides as a partially-
      competetive probe RB516A-3-P-9 complement to A allele

<400> SEQUENCE: 24
ctgagccaat tcatggacca gaacaacccg c                                  31

<210> SEQ ID NO 25
<211> LENGTH: 35
<212> TYPE: DNA
<213> ORGANISM: Artificial Sequence
<220> FEATURE:
<223> OTHER INFORMATION: Designed oligonucleotides as a partially-
      competetive probe RB516A-3-P-10 complement to A allele

<400> SEQUENCE: 25
gctgagccaa ttcatggacc agaacaaccc gctgt                              35
```